US010869746B2

(12) United States Patent
Nguyen et al.

(10) Patent No.: US 10,869,746 B2
(45) Date of Patent: Dec. 22, 2020

(54) SYSTEMS AND METHODS FOR INCONTINENCE CONTROL

(71) Applicant: SOFT HEALTH TECHNOLOGIES, LLC, Laguna Beach, CA (US)

(72) Inventors: John Nguyen, Irvine, CA (US); John M. Taylor, Trabuco Canyon, CA (US); Thomas J. Berryman, Laguna Beach, CA (US)

(73) Assignee: Soft Health Technologies, LLC, Laguna Beach, CA (US)

( * ) Notice: Subject to any disclaimer, the term of this patent is extended or adjusted under 35 U.S.C. 154(b) by 71 days.

(21) Appl. No.: 16/235,423

(22) Filed: Dec. 28, 2018

(65) Prior Publication Data

US 2019/0380819 A1    Dec. 19, 2019

Related U.S. Application Data

(63) Continuation of application No. 15/462,222, filed on Mar. 17, 2017, now abandoned.

(51) Int. Cl.
| *A61F 2/00* | (2006.01) |
| *A61F 13/472* | (2006.01) |
| *A61F 13/15* | (2006.01) |
| *A61F 13/45* | (2006.01) |
| *A61F 13/82* | (2006.01) |

(52) U.S. Cl.
CPC ............ *A61F 2/0009* (2013.01); *A61F 13/45* (2013.01); *A61F 13/47209* (2013.01); *A61F 13/47227* (2013.01); *A61F 13/47236* (2013.01); *A61F 13/82* (2013.01); *A61F 2013/15121* (2013.01); *A61F 2210/0061* (2013.01); *A61F 2210/0076* (2013.01); *A61F 2250/0078* (2013.01)

(58) Field of Classification Search
CPC .......... A61F 2/0009; A61F 2013/15097; A61F 2013/15121; A61F 13/472; A61F 13/47209; A61F 13/47227; A61F 13/47236
See application file for complete search history.

(56) References Cited

U.S. PATENT DOCUMENTS

| 4,593,053 A | 6/1986 | Jevne et al. |
| 5,074,855 A | 12/1991 | Rosenbluth et al. |

(Continued)

OTHER PUBLICATIONS

Brubaker, L., Harris, T., Gleason, D., Newman, D., North, B., Miniguard Investigation Group, "The External Urethral Barrier for Stress Incontinence: A Multicenter Trial of Safety and Efficacy", Obstetrics & Gynecology, Jun. 1999, pp. 932-937, vol. 93, No. 6, Elsevier, New York, USA.

*Primary Examiner* — Thaddeus B Cox
(74) *Attorney, Agent, or Firm* — Blair Walker IP Services, LLC

(57) ABSTRACT

A system for managing female incontinence includes a body of biocompatible material configured to fit between the labia minora and the vestibule floor, the body having a surface configured to occlude the urethral meatus, a first adhesive layer disposed on at least a first portion of the surface and configured to provide a sealing engagement between the body and the urethral meatus, and a second adhesive layer disposed over the first adhesive layer and configured to provide a sealing engagement between the body and the urethral meatus, wherein the second adhesive layer is removable from the first adhesive layer.

20 Claims, 11 Drawing Sheets

(56) References Cited

U.S. PATENT DOCUMENTS

| | | |
|---|---|---|
| 5,171,302 A | 12/1992 | Buell |
| 5,197,959 A | 3/1993 | Buell |
| 5,270,358 A | 12/1993 | Asmus |
| 5,295,983 A | 3/1994 | Kubo |
| 5,336,208 A | 8/1994 | Rosenbluth et al. |
| 5,735,835 A | 4/1998 | Holland |
| 5,769,091 A | 6/1998 | Simon et al. |
| 5,813,973 A | 9/1998 | Gloth |
| 5,885,204 A | 3/1999 | Vergano |
| 5,885,265 A | 3/1999 | Osborn, III et al. |
| 5,927,282 A | 7/1999 | Lenker et al. |
| 5,964,689 A | 10/1999 | McFall et al. |
| 6,123,693 A | 9/2000 | Osborn, III |
| 6,131,575 A | 10/2000 | Lenker et al. |
| 6,355,022 B1 | 3/2002 | Osborn, III et al. |
| 6,432,096 B1 | 8/2002 | McFall et al. |
| 6,461,340 B1 | 10/2002 | Lenker et al. |
| 6,613,955 B1 | 9/2003 | Lindsay et al. |
| 7,033,342 B2 | 4/2006 | Mizutani et al. |
| 7,074,214 B2 | 7/2006 | Mizutani et al. |
| 7,179,951 B2 | 2/2007 | Krishnaswamy-Mirle et al. |
| 7,354,425 B2 | 4/2008 | Mizutani et al. |
| 7,601,146 B2 | 10/2009 | Mizutani et al. |
| 7,686,793 B2 | 3/2010 | Mizutani et al. |
| 8,684,008 B2 | 4/2014 | St. Anne |
| 9,408,684 B2 | 8/2016 | Berryman et al. |
| 9,555,151 B2 | 1/2017 | Taylor et al. |
| 2001/0021833 A1 | 9/2001 | Schmidt et al. |
| 2001/0026810 A1 | 10/2001 | McGhee et al. |
| 2003/0100877 A1 | 5/2003 | Erdman |
| 2003/0191442 A1 | 10/2003 | Bewick-Sonntag et al. |
| 2004/0044319 A1* | 3/2004 | Bewick-Sonntag ........ A61F 13/51305 604/360 |
| 2004/0147892 A1 | 7/2004 | Mizutani et al. |
| 2004/0158222 A1* | 8/2004 | Mizutani ........... A61F 13/15577 604/385.17 |
| 2004/0266302 A1 | 12/2004 | DiSalvo et al. |
| 2008/0077081 A1 | 3/2008 | Mounce et al. |
| 2009/0182296 A1 | 7/2009 | Dennis et al. |
| 2009/0221980 A1 | 9/2009 | Mosbacher et al. |
| 2010/0198177 A1 | 8/2010 | Yahiaoui et al. |
| 2011/0008277 A1 | 1/2011 | Bruggeman et al. |
| 2011/0086077 A1 | 4/2011 | McCrea et al. |

\* cited by examiner

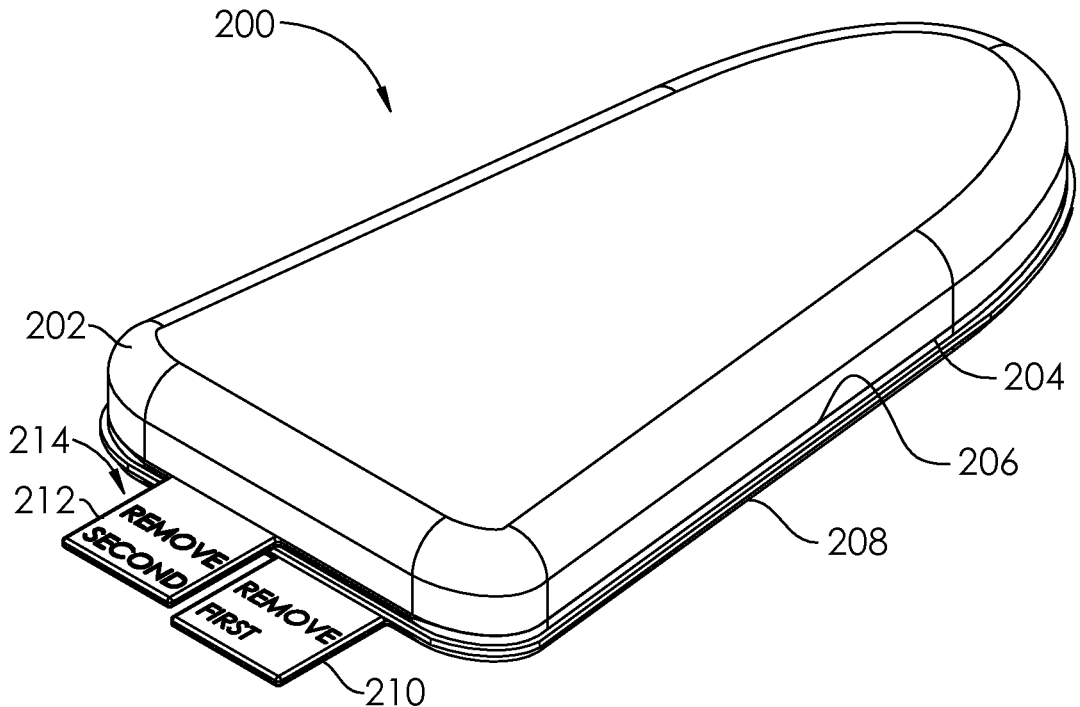
FIG. 8
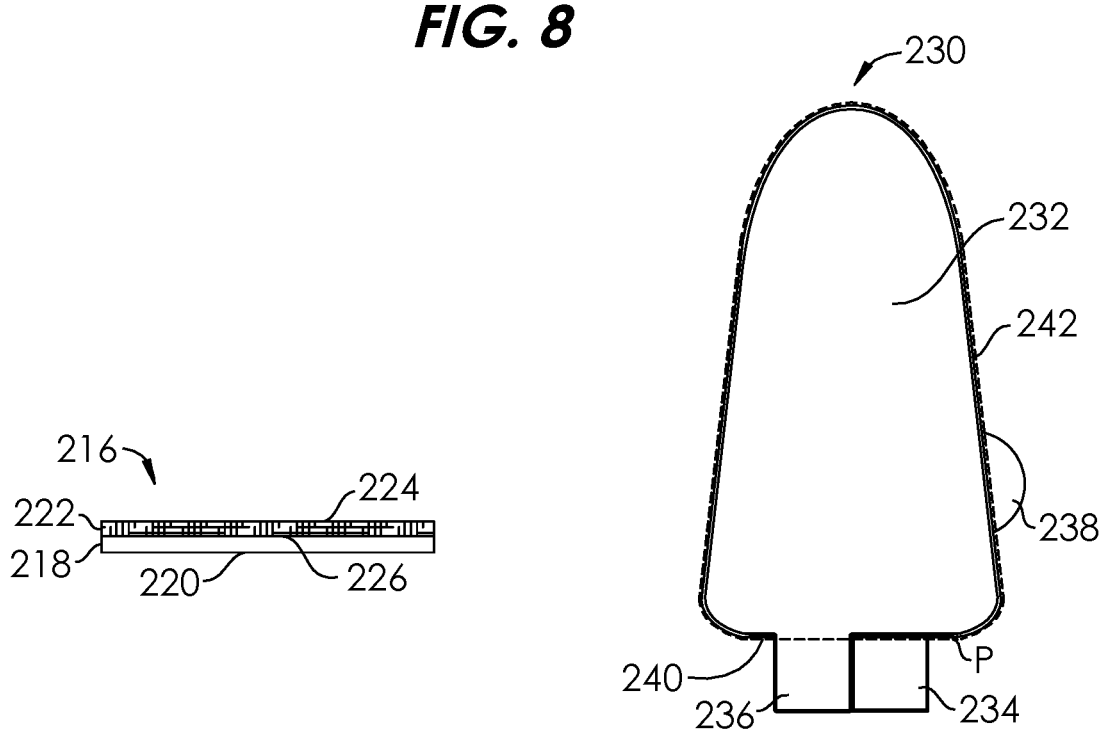
FIG. 9  FIG. 10

SYSTEMS AND METHODS FOR INCONTINENCE CONTROL

INCORPORATION BY REFERENCE TO ANY PRIORITY APPLICATIONS

This application is a continuation of U.S. patent application Ser. No. 15/462,222, filed on Mar. 17, 2017, now abandoned, which is incorporated by reference in its entirety herein for all purposes. Priority is claimed pursuant to 35 U.S.C. § 120.

FIELD OF THE INVENTION

The field of the invention generally relates to devices for treating urinary incontinence.

BACKGROUND

Urinary incontinence is a troublesome problem for many individuals. Urinary stress incontinence is a particular form of urinary incontinence wherein a physical occurrence may cause unwanted leakage of urine. For example, a sudden spike in abdominal pressure from sneezing, coughing or exercise may exceed the resistive pressure of the urethra for a brief moment, causing an involuntary leakage of urine. Stress urinary incontinence occurs predominantly in adult women, but may also occur in certain male or in younger females.

Absorbent pads are available which absorb urine after it has leaked and contain it within the wearer's undergarments. Adult diapers or absorbent panties or underwear may also be used to absorb the urine. Plastic pants designed to fit over undergarments are another means of protecting outer clothing for urine which has leaked. All of these products have the disadvantage of being forced to contain the wetness and odor of leaked urine.

More recently, urinary incontinence patches which are adhesively applied directly over the urethral meatus have been used in women with the intent of more completely sealing the urethra, and preventing the involuntary leakage of urine.

SUMMARY OF THE INVENTION

In a first embodiment of the present disclosure, a system for managing female incontinence includes a body of biocompatible material configured to fit between the labia minora and the vestibule floor, the body having a surface configured to occlude the urethral meatus, a first adhesive layer disposed on at least a first portion of the surface and configured to provide a sealing engagement between the body and the urethral meatus, and a second adhesive layer disposed over the first adhesive layer and configured to provide a sealing engagement between the body and the urethral meatus, wherein the second adhesive layer is removable from the first adhesive layer.

In another embodiment of the present disclosure, a system for managing female incontinence includes a body of biocompatible material configured to fit between the labia minora and the vestibule floor, the body having a surface configured to occlude the urethral meatus, and a first adhesive layer configured to be coupled to at least a first portion of the surface so as to provide a sealing engagement between the body and the urethral meatus, wherein the first adhesive layer, when coupled to the at least a first portion of the surface is configured to be removable from the surface.

In still another embodiment of the present disclosure, a system for managing female incontinence includes a body of biocompatible material configured to fit between the labia minora and the vestibule floor, the body having a longitudinal axis, a ventral side configured to occlude the urethral meatus, and a dorsal side, an adhesive carried on the ventral side and configured to provide a sealing engagement between the body and the urethral meatus, and a sheet having a first end and a second end, the first end coupled to the body adjacent the dorsal side of the body and the second end configured to be free from the body, wherein the second end is configured to be grasped by a user in order to apply a removal force on the body to separate the body from the urethral meatus.

In yet another embodiment of the present disclosure, a system for managing female incontinence includes a body of biocompatible material configured to fit between the labia minora and the vestibule floor, the body comprising a ventral side having an adhesive carried thereon and a dorsal side, and a removable adhesive layer carried on the ventral side of the body over the adhesive, the removable adhesive layer comprising a first adhesive surface configured to provide a sealing engagement between the body and the urethral meatus and a first release liner disposed between the first adhesive surface and the adhesive of the body, wherein the removable adhesive layer is removable from the body.

In still another embodiment of the present disclosure, a system for managing female incontinence includes a body of biocompatible material configured to fit between the labia minora and the vestibule floor, the body having a surface configured to occlude the urethral meatus, a first adhesive layer disposed on at least a first portion of the surface and configured to provide a sealing engagement between the body and the urethral meatus, and a first sheet having a first portion and a second portion, the first portion of the first sheet coupled to the body and the second portion of the first sheet extending from a dorsal side of the body, opposite a ventral side of the body containing the surface of the body, wherein the second portion of the first sheet is configured to be grasped by a user in order to apply a removal force on the body to separate the body from at least one of the urethral meatus and the vestibule floor.

In yet another embodiment of the present disclosure, a method for producing a system for managing female incontinence includes obtaining a first sheet having a first surface and a second surface, obtaining a second sheet having a first portion and a second portion, coupling the first portion of the second sheet to the first sheet, such that the second portion of the second sheet extends from the second surface of the first sheet, and wherein the first sheet is configured to fit between the labia minora and the vestibule floor and the first surface of the first sheet is configured to occlude the urethral meatus.

BRIEF DESCRIPTION OF THE DRAWINGS

FIG. 8 is a perspective view of a system for controlling urinary incontinence according to an embodiment of the present disclosure.

FIG. 9 is a side view of an adhesive layer of the system for controlling urinary incontinence of FIG. 8.

FIG. 10 is a plan view of a system for controlling urinary incontinence according to an embodiment of the present disclosure.

DETAILED DESCRIPTION

Figure 1:
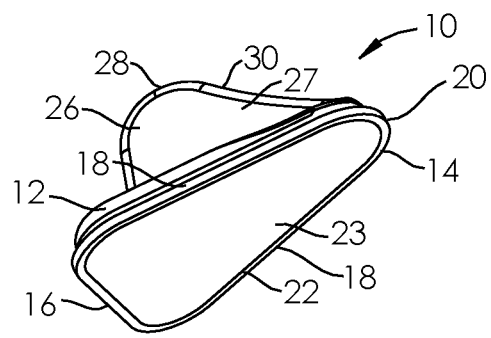
FIG. 1 is a perspective view of a female urinary incontinence device.
Figure 2:
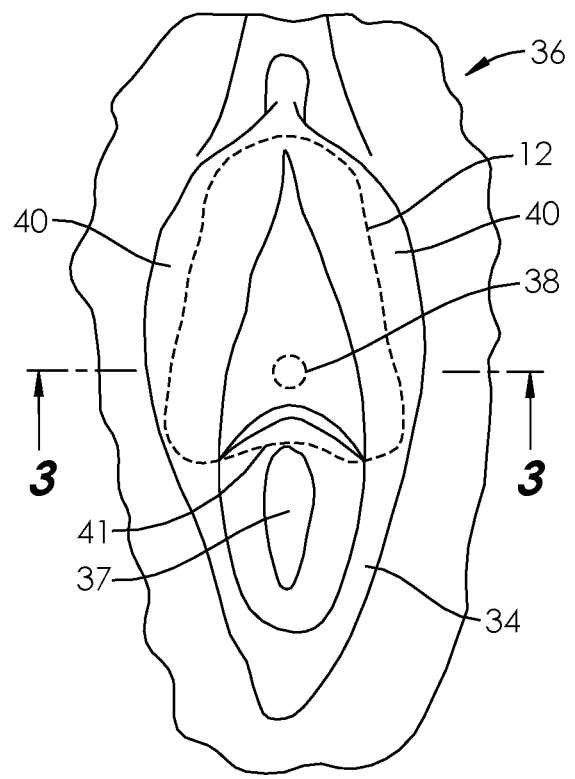
FIG. 2 is plan view of an embodiments of the device of FIG. 1, showing the device installed in the external genitalia of a human female.
Figure 3:
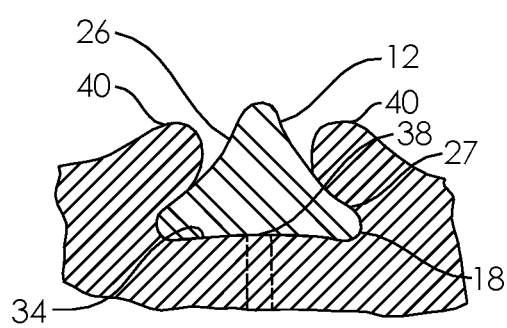
FIG. 3 is a cross-sectional view taken along line 3-3 of FIG. 2.

Referring first to FIGS. 1 through 3 of the drawings, a female urinary incontinence device 10, in accordance with a first embodiment, is shown. Any of the subsequent embodiments herein may incorporate materials, configurations, manufacturing methods, and uses described in relation to the embodiment of FIGS. 1 through 3. The device comprises a body 12, formed of a resilient foam material that is biocompatible. One suitable class of materials is that of foams formed from the water actuation of prepolymers based on either toluene diisocyanate (TDI) or methylene diphenyl diisocyanate (MDI). Such prepolymers are marketed by the Dow Chemical Company, Midland, Mich., under the trademarks "HYPOL" (TDI), "HYPOL PLUS" (MDI) and "HYPOL 2002" (TDI and MDI). Other foam materials which may be used to produce the body 12 include polyurethane foam (such as HYPOL 6000), polyvinyl chloride foam, or polyolefin foam. In some embodiments, a polyvinyl chloride foam may be utilized, such as Gaska® tape supplied by Gaska Tape, Inc., Elkhart, Ind., USA, and may have a density of between about 80 kg/m$^3$ and about 160 kg/m$^3$, or in other embodiments between about 95 kg/m$^3$ and about 130 kg/m$^3$, or in other embodiments, about 112 kg/m$^3$. In some embodiments, a polyolefin foam may be utilized, such as Softlon™ or Volara® foams, supplied by Sekisui Voltek LLC Corporation, Lawrence, Mass., USA.

Alternatively, the body 12 can be made of a biodegradable material, such as a cellulose or cotton fiber. A polyurethane foam can also be used, being rendered biodegradable by hydrolysis of a weak backbone link, such as an amine group. Other foam materials, such as polyolefins, can be used and made hydrolytically biodegradable by using weak links such as starches in the polymer backbones. In some embodiments, the foam may have a substantially thick skin, to allow increased handling, which is appropriate for the embodiments described herein which may increase the total amount of handling of the body 12.

The body 12 includes a base 14 that has the general outline of a blunt arrowhead. In some embodiments, the base may also be slightly concave. In other embodiments, the base 14 can be made slightly convex, for example, for those users who might find such a configuration more comfortable to wear. The base 14 may have a concave, convex, or neutral posterior end 16, as shown in FIG. 1, with lateral edges 18 that taper slightly toward each other as they extend toward a rounded anterior end 20. The anterior end 20 may be somewhat narrower than the posterior end 16, as shown in FIG. 1.

The body 12 is provided with an adhesive surface 23 for retention against the floor of the vestibule 34 of the vulva 36 as described in relation with FIGS. 2 and 3. In this embodiment, the base 14 is coated with an adhesive layer 22, comprising a pressure-sensitive, hydrophilic hydrogel adhesive material. Such hydrogel adhesives are marketed by R & D Medical Products, Lake Forest, Calif., USA, under the trademark "PROMEON". In other embodiments, other hydrogel adhesives may be utilized, including those supplied by Axelgaard Manufacturing Company Ltd. Located in Fallbrook, Calif., USA, including those comprising a polyacrylate copolymer. The hydrogel composition may include from about 25 to about 50 weight percent polyvinyl pyrrolidone (PVP) or about 30 to about 40 weight percent. The polyvinyl pyrrolidone may have a weight average molecular weight in the range of about 100,000 to 600,000, or in the range of about 300,000 to 400,000. A suitable polyvinyl pyrrolidone is type NP-K90 commercially available from Irvine Scientific, Santa Ana, Calif.

The composition may also include polyvinyl alcohol (PVA) in a weight percentage of about 2 to about 5 or about 3 to about 4 weight percent. A particular polyvinyl alcohol is sold by the E. I. DuPont de Nemours & Co. under the trade designation "Elvanol HV". Generally speaking, polyvinyl alcohol suitably may have a weight average molecular weight in the range of about 150,000 to about 300,000, or about 170,000 to about 220,000. A particular PVA is the material available from E. I. du Pont de Nemours & Co. having a stated molecular weight of about 185,000.

The polyvinyl alcohols may be generally at least about 75% hydrolyzed. PVA may be about 100% hydrolyzed.

The composition may also include about 5 to about 40 weight percent, or about 15 to about 25 weight percent polar plasticizer or humectant e.g., glycerol. Other useful polar plasticizers include propylene glycol, sorbitol, poly(ethylene)glycol, for example having a molecular weight in the range of about 200 to about 20,000, or polypropylene glycol, for example having a molecular weight in the range of about 500 to about 5,000. Other polar plasticizers or humectants will be well-known to one skilled in the hydrogel art.

The composition may also include the presence of about 3 to about 50 weight percent water in the resulting matrix. Deionized water is may be used. This percentage of water may provide suitable adhesiveness, tack, cohesive strength, and skin-compatibility.

One skilled in the art will recognize that it is possible to add small amounts of other materials to adjust the properties of the present composition for a particular end use. For example, if it is chosen to increase the tackiness of the gel, poly-2-acrylamido 2-methyl propane sulfonic acid poly (AMPS) (or its salts) may be employed. Other material which can be employed to increase tackiness include polyacrylic acid, polystyrene sulfonic acid or salts thereof, karaya, xanthan, guar or locust bean gums. Tackifiers above described may generally be present in the range of about 2 to about 20 weight percent.

For some applications, it may be chosen to increase the internal coherence, cohesiveness or strength of the present biomedical composition. In such instances, materials such as hydroxy propyl methyl cellulose, carboxymethyl cellulose, hydroxy propyl guar, dextran or silica may be added. One skilled in the art will recognize other materials which could be added to the composition described herein to adjust various desired properties. Generally speaking, such additives may be present in the range of about 0 to about 10 weight percent.

For preparation of the materials, generally speaking, a temperature-controlled, stirrable reactor may be employed. The reactor may be preheated to about 90° C., set to mix at approximately 100 revolutions per minute, and the following materials (in representative quantities):
1. deionized H$_2$O—39 weight percent
2. glycerol polar plactizers (Mallinckrodt, Inc.)—22 weight percent
3. polyvinyl alcohol (duPont Elvanol HV)—4 weight percent
4. polyvinyl pyrrolidone (R & D Medical Products)—35 weight percent would be mixed, for example in the order indicated. The temperature of the closed mixer then would be increased to approximately 130° C. while maintaining stirring. After a temperature of approximately 130° C. is obtained, the temperature of the mixture would be decreased to approximately 95° C., the mixer subsequently turned off and the material poured onto a release paper (e.g., "Polyslick"), the gel thereby being cooled to a solid, non-liquid state.

Another type of adhesive that has shown good results is a mixture of poly 2-hydroxyethyl methacrylate (PHEMA) and polyethylene glycol (PEG) as a plasticizer, or general material to modify bulk characteristics. The percentage of PHEMA may range from about 45% to about 75%, with a corresponding range of PEG of about 55% to about 25%. A particular composition is about 53% to about 54% PHEMA and about 47% to about 46% PEG. Lower percentages of PHEMA yield greater adhesiveness, while higher percentages of PHEMA yield greater durability. The PEG may have a molecular weight between about 400 and about 1000. The PHEMA may be a mixture of low molecular weight PHEMA (molecular weight between about 10,000 and about 100,000) and high molecular weight PHEMA (molecular weight greater than about 100,000). The low molecular weight PHEMA provides adhesive properties, while the high molecular weight PHEMA improves adhesive structural integrity. The PHEMA mixture may be between about 10% to about 50% low molecular weight PHEMA and between about 90% and about 50% high molecular weight PHEMA, with the precise mixture being determined by the particular adhesive properties desired.

While a possible plasticizer is PEG, as described above, other plasticizers can be used, such as propylene glycol, polypropylene glycol (PPG), or glycerin.

If the body 12 is made of TDI or MDI, the material of the body 12 itself can be rendered adhesive by combining the TDI or MDI one-to-one by weight with about 0.25 to about 0.50 molar ammonium hydroxide during the water actuation of the foam. The resulting material has a surface that is positively charged, so that it will adhere to a negatively-charged mucoid surface (such as the surface of the vestibule 34 and the inner portions of the labia minora 40).

Alternatively, the entire body 12 can be formed of an adhesive, such as the PHEMA/PEG mixture described above. In many medical or body contact applications, a PHEMA is used which is made from an optical grade HEMA monomer. This optical grade HEMA monomer may, for example, have a purity of 99% and be expensive to produce and acquire. In the embodiments described within, PHEMA made from a HEMA monomer having a purity of between about 96% to about 98% can be used with good results.

The side of the body 12 opposite the base 14 includes a central longitudinal ridge 26 which forms the thickest part of the body 12. The ridge 26 may also be described as a fin. If one adopts the convention that the base 14 is the "bottom" of the body 12, then the body 12 can be defined as having a surface 27 opposite the base that slopes "downwardly" from either side of the ridge 26 toward the edges 18, so that there is a gradual reduction in body 12 thickness from the ridge 26 to the edges 18. Viewed another way, the body 12 can be defined as having a cross-sectional shape that narrows from the base 14 to the "top" or apex 28 of the ridge 26. The resulting configuration is such that a lateral cross section of the body 12, taken through the ridge 26, produces a shape resembling a triangle with rounded corners and slightly concave sides, as shown in FIG. 3. Similarly, the ridge 26 has an anterior edge 30 that tapers "downwardly" from the apex 28 toward anterior end 20 of the body 12, as shown in FIG. 1, so that the anterior end 20 of the body 12 is substantially reduced in thickness as compared to the posterior end 16.

The female urinary incontinence device 10 may be provided with a handle or tab that is either integrally molded with the body 12, or subsequently attached to it. In some embodiments, the handle may be a ring or loop, for example of thread, that is inserted laterally through the body 12. The loop may be located near the anterior portion of the apex 28 of the ridge 26, depending on the embodiment. In other embodiments, the handle may comprise a tubular portion configured to receive a finger of the user, to aid in the removal of the female urinary incontinence device 10. In other embodiments, a tether may be coupled to the body 12, to aid in the removal of the female urinary incontinence device 10. Any of these elements (ridge, fin, handle, tab, ring, loop, tether) may be generally described as manipulation members or manipulation elements. Other embodiments of manipulation elements that may be used are described in U.S. Pat. No. 9,408,648, issued Aug. 9, 2016, and entitled "Systems and Methods for Incontinence Control," which is hereby incorporated by reference in its entirety for all purposes.

FIGS. 2 and 3 show the female urinary incontinence device 10 installed in the external genitalia of a human female. The female urinary incontinence device 10 is installed so that the base 14 is seated against the vestibule 34 of the vulva 36, anteriorly of the vaginal orifice 37, thereby occluding the urethral meatus 38. The adhesive surface 23, provided by the adhesive layer 22 on the base 14, is configured to seal the urethral meatus 38 to prevent the escape of urine. The lateral edges 18 and the anterior end 20 of the body 12 are tucked under the labia minora 40. The engagement between the labia minora 40 and the sloping surface 27 enhances the retention of the body 12 in engagement with the vestibule 34. A concavity 41 (FIG. 2) in the posterior end 16 of the body 12 allows for somewhat greater surface area for engagement by the labia minora 40, while leaving a clearance for the vaginal opening 37. The ridge 26 extends into the interlabial space, and is configured to be exposed to facilitate manual grasping, for removal of the female urinary continence device 10.

The body 12 can be provided in a number of sizes to fit a large variety of individuals. The length of the body 12 can be made to be approximately the same as the distance between the anterior lip of the vaginal orifice and the juncture of the labia minora 40. The width of the body 12 may be chosen to conform substantially to the width of the vestibule 34. Predetermined sizes can be trimmed individually for optimum fit. In some cases, a mold of the relevant portions of the vulva may be taken prior to sizing the pad.

The adhesive layer 22 not only provides a fluid-tight seal for the urethral meatus 38, but it also minimizes slippage of the female urinary incontinence device 10. The central ridge 26 lends rigidity that resists deformation of the body 12 and rupture of the adhesive layer 22 under fluid pressure from the urethra, thereby enhancing the fluid-tight seal provided by the body 12 against the urethral meatus 38. It may be chosen to extend the adhesive layer 22 onto the labia-engaging surface 27, thereby further enhancing the stability of the female urinary incontinence device 10.

A female urinary incontinence device 10 constructed in accordance with the first embodiment, as described above, can be made to withstand short-term fluid pressures from the urethra in the range of up to at least about 100, and preferably about 170, centimeters of water without significant leakage, as least for a short period of time. For example, for about two seconds or greater, and preferably about three seconds or greater. Pressures on this order are those that would typically result in involuntary urine voiding in cases of stress and urge incontinence. 170 centimeters of water is the approximate maximum bear-down pressure for a typical adult human female.

As an option, the foam material of the body 12, and/or the adhesive surface 23, can be provided with a medically-active composition. An antibacterial or germicidal agent, such as silver oxide or silver azide may be used, for example.

In some embodiments, one or more portions of the female urinary incontinence device 10 may be biodegradable, and may be configured for flushing down toilets or in conventional sewer systems.

In some embodiments, the female urinary incontinence device 10 may include a substance, for example, either directly on the body 12 or on the adhesive layer 22, wherein the substance is configured for controlling the odor of the area associated with both the urethral area and the vaginal area of the wearer. The substance may be configured to lessen, block, mask or completely eliminate one or more types of odors in the area associated with either the urethral area or the vaginal area of the wearer. In some embodiments, the substance may be configured to control vaginal-created odors, for example, odors associated with vaginal discharge. In some embodiments, the substance may be configured to control urethra-created odors, for example urethral tract odor. In some embodiments, the substance may be configured to control sweat gland-created odors. In some embodiments, the substance may be configured to control a combination of these odors. Substances for odor control which may be used are described in U.S. Pat. No. 9,408,648, issued Aug. 9, 2016, and entitled "Systems and Methods for Incontinence Control."

In some embodiments, the female urinary incontinence device 10 may include a substance, for example, either directly on the body 12 or on the adhesive layer 22, wherein the substance is configured for medical treatment. In some embodiments, the substance is configured for treatment of vaginal disorders. In some embodiments, the substance is configured for treatment of urethral disorders. In some embodiments, the substance is configured for treatment of reproductive disorders. In some embodiments, the substance is configured as a birth control treatment. In some embodiments, the substance is configured for treatment of dermatological disorders. In some embodiments, the substance is a drug. Substances for medical treatment which may be used are described in U.S. Pat. No. 9,408,648, issued Aug. 9, 2016, and entitled "Systems and Methods for Incontinence Control."

Other types of gels may be incorporated into the body 12 and/or the adhesive layer 22, including other types of hydrogels. In some embodiments, the female urinary incontinence device 10 may comprise a silicone hydrogel. In some embodiments, the silicone hydrogel may comprise a water gradient silicone hydrogel, which, when hydrated, has a first water content at a first portion of the female urinary incontinence device 10 and a second water content at a second portion of the female urinary incontinence device 10. Exemplary silicone hydrogels which may be used are described in U.S. Pat. No. 9,555,151, issued Jan. 31, 2017, and entitled "Systems and Methods for Incontinence Control," which is hereby incorporated by reference in its entirety for all purposes.

Silicone hydrogels and methods for forming devices from silicone hydrogels may be used in certain embodiments, such as those described in U.S. Publication No. 2012/

0026458, filed Jul. 29, 2011, and entitled "Silicone Hydrogel Lenses with Water-Rich Surfaces," which is hereby incorporated by reference in its entirety for all purposes. Silicone hydrogels and methods for forming devices from silicone hydrogels may be used in certain embodiments, such as those described in U.S. publication No. 2015/0094393, filed Sep. 23, 2014, and entitled "Method for Making UV-Absorbing Ophthalmic Lenses," which is hereby incorporated by reference in its entirety for all purposes.

Materials and methods for forming devices may be used in certain embodiments, such as those described in U.S. Pat. No. 5,508,317, filed Aug. 4, 1994, and entitled, "Photocrosslinked Polymers," which is hereby incorporated by reference in its entirety for all purposes. Materials and methods for forming devices may be used in certain embodiments, such as those described in U.S. Pat. No. 6,800,225, filed Jul. 14, 1994, and entitled, "Process and Device for the Manufacture of Mouldings and Mouldings Manufactured in Accordance with that Process," which is hereby incorporated by reference in its entirety for all purposes. Materials and methods for forming devices may be used in certain embodiments, such as those described in U.S. Pat. No. 8,163,206, filed Jun. 16, 2009, and entitled, "Method for Making Silicone Hydrogel Contact Lenses," which is hereby incorporated by reference in its entirety for all purposes.

Figures 4, 5:
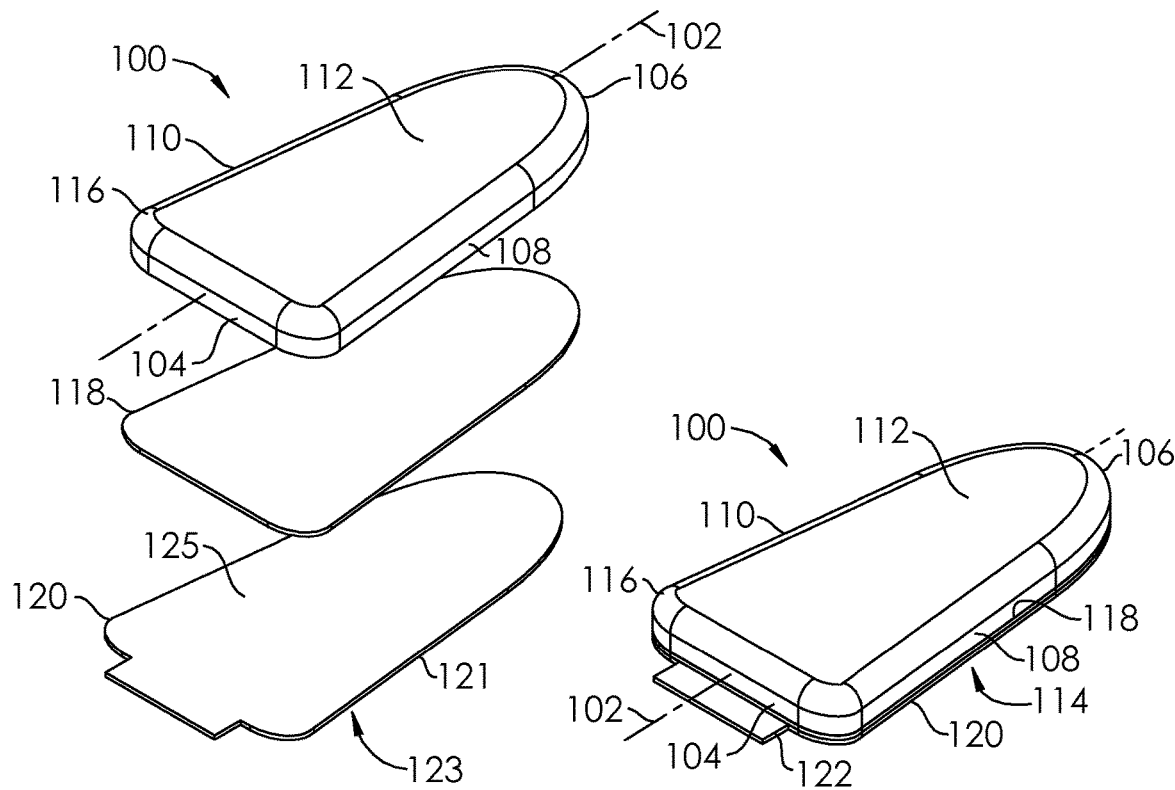
FIG. 4 is an exploded perspective view of a system for controlling urinary incontinence according to an embodiment of the present disclosure.
FIG. 5 is a perspective view of the system for controlling urinary incontinence of FIG. 4.

FIGS. 4 and 5 illustrate a system for controlling urinary incontinence 100 having a longitudinal axis 102, a posterior end 104, an anterior end 106, a left lateral end 108, a right lateral end 110, a dorsal side 112, and a ventral side 114. The terms "left" and "right" are chosen to coincide with alignment with the sides of the user when the system for controlling urinary incontinence 100 is being worn by the user. The system for controlling urinary incontinence 100 may be constructed from any of the materials described in relation to the female urinary incontinence device 10 of FIG. 1. The system for controlling urinary incontinence 100 includes a body 116 of biocompatible material which is configured to fit between the labia minora 40 and the vestibule floor 34 of a vulva 36 of a subject. The body 116, as in the other embodiments herein, is configured to occlude the urethral meatus 38 of the subject. A first adhesive layer 118 is carried on the body 116, and a second adhesive layer 120 is carried on the first adhesive layer 118. The second adhesive layer 120 is configured to be removable from the first adhesive layer 118. In one embodiment, the second adhesive layer 120 is configured to be removed from the first adhesive layer 118 without causing the first adhesive layer 118 to be removed from the body 116. In some embodiments, the first adhesive layer 118 is configured to be removable from the body 116. In other embodiments, the first adhesive layer 118 is configured to be permanently attached to the body 116. The second adhesive layer 120 includes a ventral adhesive surface 123, and may include a release liner on its dorsally-oriented side 125 to lessen the force at which the second adhesive layer 120 must be peeled from the first adhesive layer 118. Any of the removable adhesive layers described in other embodiments herein may incorporate a similar release liner. Further description of release liners is subsequently given in relation to FIG. 9. Alternatively, instead of having a release liner, the second adhesive layer 120 may be treated on its dorsally-oriented side 125 to lower its relative tackiness, thus lowering the peel force between the second adhesive layer 120 and the first adhesive layer 118.

FIG. 4 represents an exploded illustration of the system for controlling urinary incontinence 100 shown in FIG. 5. In some embodiments, the system for controlling urinary incontinence 100 is packaged and sold in the configuration illustrated in FIG. 5. In other embodiments, the body 116, the first adhesive layer 118, and the second adhesive layer 120 are each packaged and sold separately. In other embodiments, the body 116, the first adhesive layer 118, and the second adhesive layer are packaged separately, but sold together, for example, within a main package. In some embodiments, the body 116 and first adhesive layer 118 are packaged together, and the second adhesive layer 120 is packaged separately. In some embodiments, a user may prepare the system for controlling urinary incontinence 100 shown in FIG. 2 by placing the second adhesive layer 120 onto the first adhesive layer 118.

In any of these configurations or strategies, the second adhesive layer 118, as shown in FIG. 2, is configured to provide a sealing engagement between the body 116 and the urethral meatus 38, as described in relation to FIGS. 1-3. The first adhesive layer 118 is an intermediate layer between the body 116 and the second adhesive layer 120. At a particular time after the system for controlling urinary incontinence 100 is applied to a user by adhering the second adhesive layer 120 to the vestibule floor 34 and/or urethral meatus 38, the second adhesive layer 120 may lose some or all of its adhesion or other mechanical properties, for example, by becoming soiled or absorbing liquids, or simply breaking down chemically. The system for controlling urinary incontinence 100 is configured to be removed from the user, by the user or another person, and the second adhesive layer 120 is configured to be removed from the first adhesive layer 118, by the user or another person. Following removal, the system for controlling urinary incontinence 100 may be replaced on the user, by the user or another person, as the first adhesive layer 116 is configured to provide a sealing engagement between the body 116 and the urethral meatus 38, as described in relation to FIGS. 1-3. Prior art devices having a body and only one adhesive layer would have to be discarded once the single adhesive layer was no longer functioning, but the system for controlling urinary incontinence 100 may be reused, and thus has an extended life. With two adhesive layers 118, 120, the life of the system for controlling urinary incontinence 100 may be double that of a prior art single adhesive layer device. The improved efficiency thus can provide a lower cost to the user, a reduced amount of waste from packaging materials, and simpler maintenance and use for the user.

In use, the second adhesive layer 120, is the first of the two adhesive layers 118, 120 used for providing a sealing engagement between the body 116 and the urethral meatus 38. The second adhesive layer 120 also serves to cover and protect the first adhesive layer 118 until the user chooses to remove the system for controlling urinary incontinence 100, remove the second adhesive layer 120 from the first adhesive layer 118 (thus exposing a formerly protected adhesive surface of the first adhesive layer 118) and replace the system for controlling urinary incontinence 100, such that the first adhesive layer 118 now provides a sealing engagement between the body 116 and the urethral meatus 38. To remove any possible confusion, in the embodiment of FIG. 5, the second adhesive layer 120 is configured to be used (for sealing engagement with the urethral meatus 38 and/or the vestibule floor 34) prior to the first adhesive layer.

The words "first" and "second" are thus used for purposes of claiming the structure of the system, and are actually opposite of the order of use. However, in an alternative embodiment, it is possible to provide the body 116 and first adhesive layer 118 for use first, and then, after the first adhesive layer 118 loses its adhesion properties with the urethral meatus 38 and/or vestibule floor 34, to secure a second adhesive layer 120 (having two opposing adhesive surfaces) onto the first adhesive layer 118. Thus, the first adhesive surface of the second adhesive layer 120 would adhere to the first adhesive layer 118 and the second adhesive surface of the second adhesive layer 120 would be used for sealing engagement with the urethral meatus 38.

Returning to the embodiment of FIGS. 4 and 5, the second adhesive layer is shown having a removal feature 122 comprising a tab. Though the removal feature 122 is shown at the posterior end 104 of the system for controlling urinary incontinence 100, it may alternatively located along any portion of the perimeter 121 of the second adhesive layer 120, for example, at a location adjacent the anterior end 106, left lateral end 108, or right lateral end 110 of the system for controlling urinary incontinence 100. The removal feature 122 is configured to be engaged by the user, for example by grasping with two opposing fingers, and pulled, in order to peel the second adhesive layer 120 from the first adhesive layer 118. The first adhesive layer 118 and second adhesive layer 120 may be configured so that the peel force between the second adhesive layer 120 and the first adhesive layer 118 is less than the peel force between the first adhesive layer 118 and the body 116. This will be described in more detail in relation to FIGS. 20 and 21. Because the removal of the second adhesive layer 120 does not remove or damage the first adhesive layer 118, the system for controlling urinary incontinence 100 will function similarly in its first phase (using the second adhesive layer 120 for adhesion) and its second phase (using the first adhesive layer 118 for adhesion). To remove the second adhesive layer 120 the user may grasp the system for controlling urinary incontinence 100 by opposing fingers of a first hand on, for example, the left lateral end 108 and the right lateral end 110, and then grasp the removal feature 122 by opposing fingers of the second hand and peel the second adhesive layer 120 from the first adhesive layer 118/body 116. The peeling, when the removal feature 122 is used, proceeds from the posterior end 104 to the anterior end 106.

In the embodiment of the system for controlling urinary incontinence 100 of FIGS. 4-5, including alternative embodiments thereof, the first adhesive layer 118 and/or second adhesive layer 120 may comprise one or more of the following: a hydrogel, such as Poly(2-hydroxyethyl methacrylate) (pHEMA), or a silicone hydrogel, such as a water gradient silicone hydrogel. The body 116 may comprise a foam or a silicone hydrogel, such as a water gradient silicone hydrogel.

Figures 6, 7:
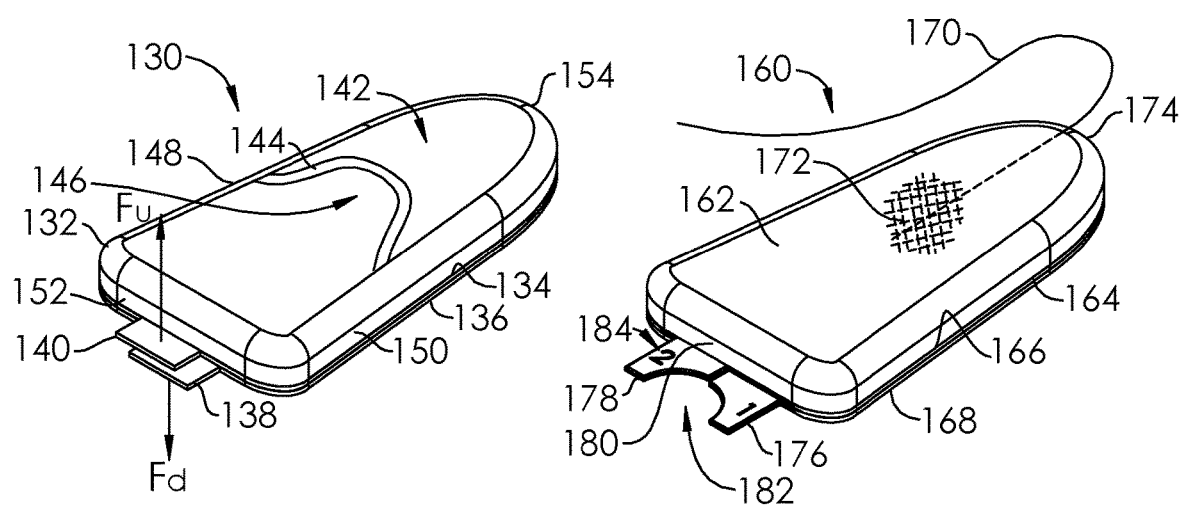
FIG. 6 is a perspective view of a system for controlling urinary incontinence according to an embodiment of the present disclosure.
FIG. 7 is a perspective view of a system for controlling urinary incontinence according to an embodiment of the present disclosure.

FIG. 6 illustrates a system for controlling urinary incontinence 130 which, like the embodiment of FIG. 5, includes a body 132, a first adhesive layer 134, and a second adhesive layer 136. The system for controlling urinary incontinence 130 may be constructed from any of the materials described in relation to the female urinary incontinence device 10 of FIG. 1. The body 132 also includes a manipulation member 142 disposed on its dorsal side 112, and comprising a wall 144 and a pocket 146. The manipulation member 142 is configured to allow a finger of the user to be inserted into the pocket 146 in order to aid the placement of the system for controlling urinary incontinence 130 in the user, or the removal of the system for controlling urinary incontinence 130 from the user. Like the embodiment of FIG. 5, the second adhesive layer 136 includes a tab 138, but additionally, the first adhesive layer 134 includes a tab 140. Again, the tabs 138, 140 are shown at the posterior end 140 of the system for controlling urinary incontinence 130, but each or both may be located anywhere around the perimeter. As shown, the tabs 138, 140 are adjacent each other, but are slightly staggered or offset, with the tab 138 being closer to the right lateral end 148 of the system for controlling urinary incontinence 130 and the tab 140 being closer to the left lateral end 150 of the system for controlling urinary incontinence 130. The staggered placement of the tabs 138, 140 allows the user, when removing the second adhesive layer 136, to grasp the tab 138 with opposing fingers of a first hand and to grasp the tab 140 with opposing fingers of a second hand. The user is then able to place a downward force $F_d$ on tab 138 while maintaining an upward force $F_u$ on tab 140. This allows the user to peel the second adhesive layer 136 from the first adhesive layer 134 without placing any significant peel force between the first adhesive layer 134 and the body 132. Thus, even in embodiments in which the peel force between the second adhesive layer 136 and the first adhesive layer 134 is not significantly less than the peel force between the first adhesive layer 134 and the body 132, the risk of inadvertently removing the first adhesive layer 134 from the body 132 is lessened or altogether removed. The peeling, with the tabs 138, 140 located as shown, proceeds from the posterior end 152 to the anterior end 154 of the system for controlling urinary incontinence 130. In some embodiments, the tabs 138, 140 may each be a separate color, in order to easily allow the user to differentiate between them. In other embodiments, the adhesive layers 134, 136 themselves may each be a separate color.

Alternatively, the user may grasp the system for controlling urinary incontinence 130 by opposing fingers of a first hand on, for example, the left lateral end 150 and the right lateral end 148, and then grasp the tab 138 by opposing fingers of the second hand and peel the second adhesive layer 136 from the first adhesive layer 134/body 132.

In the embodiment of the system for controlling urinary incontinence 130 of FIG. 6, including alternative embodiments thereof, the first adhesive layer 134 and/or second adhesive layer 136 may comprise one or more of the following: a hydrogel, such as Poly(2-hydroxyethyl methacrylate) (pHEMA), or a silicone hydrogel, such as a water gradient silicone hydrogel. The body 132 may comprise a foam or a silicone hydrogel, such as a water gradient silicone hydrogel.

FIG. 7 illustrates a system for controlling urinary incontinence 160 comprising a body 162, a first adhesive layer 164, a second adhesive layer 166, and a third adhesive layer 168. The system for controlling urinary incontinence 160 may be constructed from any of the materials described in relation to the female urinary incontinence device 10 of FIG. 1. The first adhesive layer 164 is carried on a ventral portion of the body 162, and is not configured to be removed. A manipulation member 170 comprises a tether, and is secured to the body 162 and/or the first adhesive layer 164. The manipulation member 170 may be grasped by opposing fingers to remove the system for controlling urinary incontinence 160 from the user via a tensile force which pulls on the anterior end 174. A scrim 172 or any type of fabric or sheet may be molded into the body 162 and may also be integrated or comingled with the manipulation member 170 in order to secure the manipulation member 170 well with the body 162. The fabrics or sheets may include woven fabrics or sheets, or in other embodiments, non-woven fabrics or sheets. The third adhesive layer 168 has a tab 176, and is configured to be used first and removed first. The second adhesive layer 166 has a tab 178, and is configured to be used second and removed second. The first adhesive layer 164 is configured to be used third, with the system for controlling urinary incontinence 160 configured to be discarded afterwards. Again, thought the tabs 176, 178 are shown at the posterior end 180 of the system for controlling urinary incontinence 160, they may be located at other portions of the perimeter of the system for controlling urinary incontinence 160. One advantage to being located at the posterior end 180 and not at the anterior end 174, is that the tabs may be allowed more profile (extension from the body 162), as they do not necessarily come in close contact with tissue within the labia minora 40. A relief 182 may be created in the tabs 176, 178, so that they do not interfere with or cover the vaginal opening 37.

To remove the third adhesive layer 168 from the second adhesive layer 166, the user grasps tab 178 with a first set of opposing fingers and grasps tab 176 with a second set of opposing fingers and applies opposite forces on the tabs 176, 178 to peel the third adhesive layer 168 from the second adhesive layer 166. This may even be done with a single hand, if the user has enough dexterity, for example using the thumb and index finger as the first pair of opposing fingers, and two or three of the other three fingers to apply the grasping force. To remove the second adhesive layer 166 from the first adhesive layer 164, the user grasps the body 162 with opposing fingers of a first hand and grasps the tab 178 and pulls on the tab 178 to peel the second adhesive layer 166 from the first adhesive layer 164. Text 184 can be placed on the tabs, for example, on a dorsal side (as shown), and/or on a ventral side (not visible in FIG. 7) in order to better instruct the user and identify the particular feature. Tab 176 is shown labeled with the text "1" to indicate that tab 176 is grasped when removing the first layer to be removed (third adhesive layer 168). Tab 178 is shown labeled with the text "2" to indicate that tab 178 is grasped when removing the second layer to be removed (second adhesive layer 166).

In the embodiment of the system for controlling urinary incontinence 160 of FIG. 7 including alternative embodiments thereof, the first adhesive layer 164 and/or second adhesive layer 166 and/or third adhesive layer 168 may comprise one or more of the following: a hydrogel, such as Poly(2-hydroxyethyl methacrylate) (pHEMA), or a silicone hydrogel, such as a water gradient silicone hydrogel. The body 162 may comprise a foam or a silicone hydrogel, such as a water gradient silicone hydrogel.

FIG. 8 illustrates a system for controlling urinary incontinence 200 comprising a body 202, a first adhesive layer 204, a second adhesive layer 206, and a third adhesive layer 208. The system for controlling urinary incontinence 200 may be constructed from any of the materials described in relation to the female urinary incontinence device 10 of FIG. 1. The third adhesive layer 208 includes a tab 210 containing text 214 with an instruction to the user "REMOVE FIRST." The second adhesive layer 206 includes a tab 212 containing text 214 with an instruction to the user "REMOVE SECOND." In alternate embodiments, the test 214 may include an instruction and may also include a mark (e.g., a dot or an "x") on a particular location of the tab 210, 212 that indicates where the user is to grasp the tab 210, 212. The text 214 may also have arrow or other directional indicators which instruct the user which direction to apply a force (e.g., peel force). Either of the third adhesive layer 208 or second adhesive layer 206 may include a composite structure, is seen in the generic composite adhesive layer 216 in FIG. 9. The composite adhesive layer 216 includes an adhesive material 218 having an adhesive surface 220 and a liner 222 having a liner surface 224. The adhesive material 218 and the liner 222 are coupled together at an interface 226. The interface 226 in configured to hold the adhesive material 218 and liner 222 together and to by resistant to their separation. The adhesive surface 220 of the adhesive material 218 is configured to adhere to the vestibule floor 34 and/or urethral meatus 38, but may also be configured to adhere to a liner surface 224 of another composite adhesive layer 216. The liner surface 224 of the liner 222 is configured to be engaged by an adhesive surface (such as the adhesive surface 220 of an adhesive layer 216), but is configured to allow the adhesive surface to which it is engaged to be controllably peeled away from it. The liner 222 thus operates as a release liner to further control the peeling of adhesive layers, such as the third adhesive layer 208 and second adhesive layer 206. The liner 222 may be a non-adhesive, non-tacky material, or may at least be a less-tacky material, so that it may easily be handled without sticking to a user's fingers. In some embodiments, the tab 210, 212 may simply be an extension of the liner 222, and may even be integral with the liner 222. The tabs 210, 212 and the liner 222 itself may be a non-adhesive, non-tacky material, or may at least be a less-tacky material. Thus, the tabs 210, 212 may easily be handled without sticking to a user's fingers, and the liner 222, allows controlled peeling of the third adhesive layer 208 from the second adhesive layer 206.

In some embodiments, the body 202 may have a first color and the liner 222 may have a second color, different and distinguishable from the first color, to ease the identification and the removal of the composite adhesive layer 216. In some embodiments, the body 202 may have a first color and the composite adhesive layer 216 (any part thereof) may have a second color, different and distinguishable from the first color, to ease the identification and the removal of the composite adhesive layer 216.

In some embodiments, the liner 222 comprises a polyolefin, such as a polyethylene or a polypropylene. In some embodiments, the liner 222 comprises a medium-density polyethlyne. In some embodiments, the liner 222 comprises polyester, such as polyethylene terephthalate (PET). In other embodiments, the liner 222 may comprise hemp. In some embodiments, the liner 222 may be a solid sheet and in other embodiments, the liner 222 may be a woven structure. In some embodiments, the liner 222 may be configured to be biodegradable, and may comprise cellulose. In some embodiments, the entire composite adhesive layer 216 is biodegradable, and may thus, in some cases, be flushable in a toilet when discarded.

In the embodiment of the system for controlling urinary incontinence 200 of FIG. 8 including alternative embodiments thereof, the first adhesive layer 204 and/or second adhesive layer 206 and/or third adhesive layer 208 may comprise one or more of the following: a hydrogel, such as Poly(2-hydroxyethyl methacrylate) (pHEMA), or a silicone hydrogel, such as a water gradient silicone hydrogel. The body 202 may comprise a foam or a silicone hydrogel, such as a water gradient silicone hydrogel.

FIG. 10 illustrates a system for controlling urinary incontinence 230 comprising a body 232. A perimeter P of the body 232 is shown (dotted line), and forms a general closed arrowhead shape. Tabs 234, 236 extend externally of the perimeter P at the posterior end 240. An additional tab 238 extends externally of the perimeter P at a lateral end 242. The tabs 234, 236, 238 may each be attached to a different adhesive layer, or two or more tabs may be attached to a single adhesive layer (e.g., at different locations). The system for controlling urinary incontinence 230 may be constructed from any of the materials described in relation to the female urinary incontinence device 10 of FIG. 1.

Figure 11:
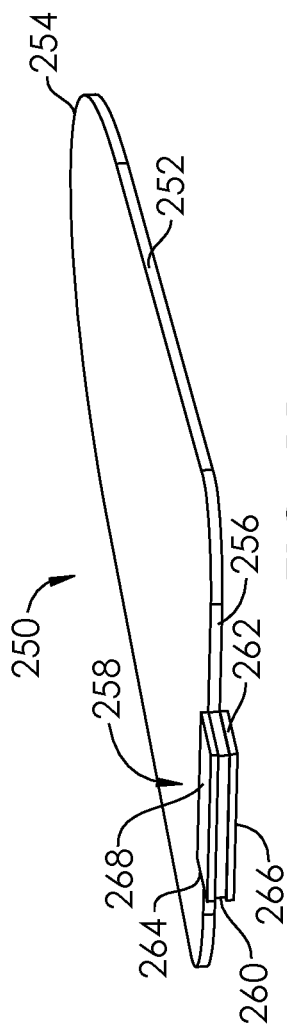
FIG. 11 is a perspective view of an adhesive layer according to an embodiment of the present disclosure.

FIG. 11 illustrates an adhesive layer 250 which may be used with the embodiments described herein. The adhesive layer 250 includes a sheet 252 of adhesive material having a first end 254 and a second end 256. The system for controlling urinary incontinence 250 may be constructed from any of the materials described in relation to the female urinary incontinence device 10 of FIG. 1. At the second end 256 a tab 258 is coupled to the sheet 252 and is configured for grasping, for example, in order to peel the adhesive layer from a system for controlling urinary incontinence. The tab 258 has an internal portion 260 which is an outward extension of the sheet 252 of adhesive material. A first block 262 is attached to the internal portion 260 at a first side, and a second block 264 is attached to the internal portion 260 at a second (opposite) side. The first block 262 includes a first non-adhesive surface 266 configured for non-stick contact by a user. The second block 264 includes a second non-adhesive surface 268 configured for non-stick contact by a user. The two non-adhesive surfaces 266, 268 allow a user to easily grasp the tab 258 of the adhesive layer 250 without it sticking to the user's fingers (or gloves). This facilitates the peeling process of the adhesive layer 250.

Figure 13:
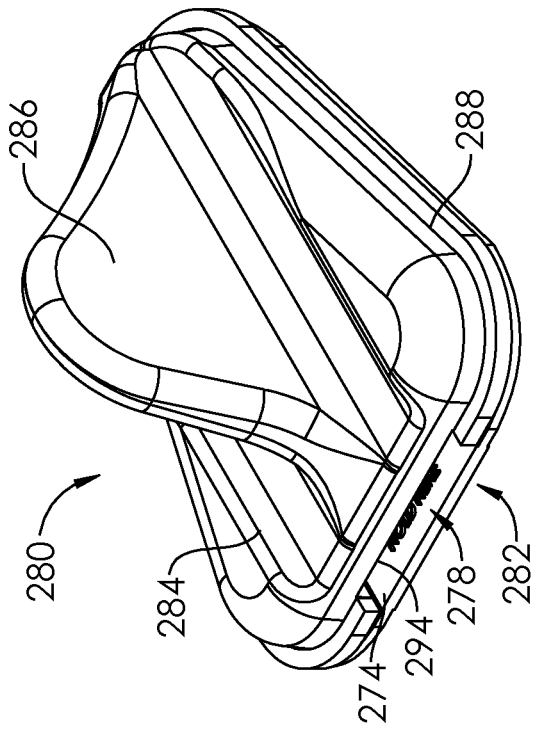
FIG. 13 is a perspective view of the system for controlling urinary incontinence of FIG. 12.
Figure 12:
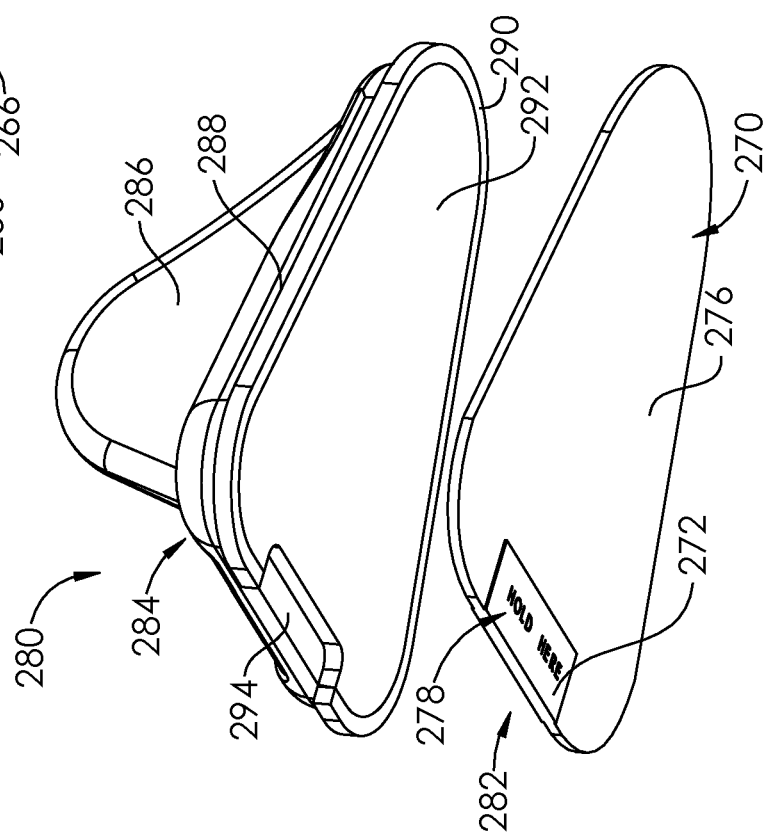
FIG. 12 is an exploded perspective view of a system for controlling urinary incontinence according to an embodiment of the present disclosure.

An adhesive layer 270, similar to the adhesive layer 250, of FIG. 11 is illustrated in FIGS. 12 and 13. The adhesive layer 270 includes a first non-stick surface 272 and a second non-stick surface 274, which are each coupled to a sheet 276 of adhesive material which comprises the adhesive layer 270. Each of the non-stick surfaces 272, 274 may be formed from a block (Or sheet) having a non-adhesive surface, or the sheet 276 of adhesive material itself may be treated to create (at that particular portion) the non-stick surface 272, 274. The first non-stick surface 272 and second non-stick surface 274 each contain text 278 which includes an instruction ("HOLD HERE") which also indicates a location for the user to grasp the first non-stick surface 272 and a second non-stick surface 274. Thus, the first non-stick surface 272 and a second non-stick surface 274 together comprise a tab 282, however, it is a tab 282 which does not extend externally of the perimeter of the footprint of the sheet 276. A system for controlling urinary incontinence 280 includes the adhesive layer 270 and a body 284 having a ridge 286, and a base 288. The system for controlling urinary incontinence 280 may be constructed from any of the materials described in relation to the female urinary incontinence device 10 of FIG. 1. The base 288 includes a surface 290 having a first adhesive layer 292. The adhesive layer 270 acts as the second adhesive layer, and thus is coupled to the first adhesive layer 292, as shown in FIG. 13. A relief 294 is formed in the base 288 (and in some embodiments, in the body 284 also). The relief 294 is located adjacent to the non-stick surface 274 and is large enough to allow at least a portion of a finger to be inserted opposite the non-stick surface 274 to ease the peeling of the (second) adhesive layer 270 from the first adhesive layer 292.

In the embodiment of the system for controlling urinary incontinence 280 of FIGS. 12 and 13, including alternative embodiments thereof, the first adhesive layer 292 and/or (second) adhesive layer 270 may comprise one or more of the following: a hydrogel, such as Poly(2-hydroxyethyl methacrylate) (pHEMA), or a silicone hydrogel, such as a water gradient silicone hydrogel. The body 284 may comprise a foam or a silicone hydrogel, such as a water gradient silicone hydrogel.

Figure 14:
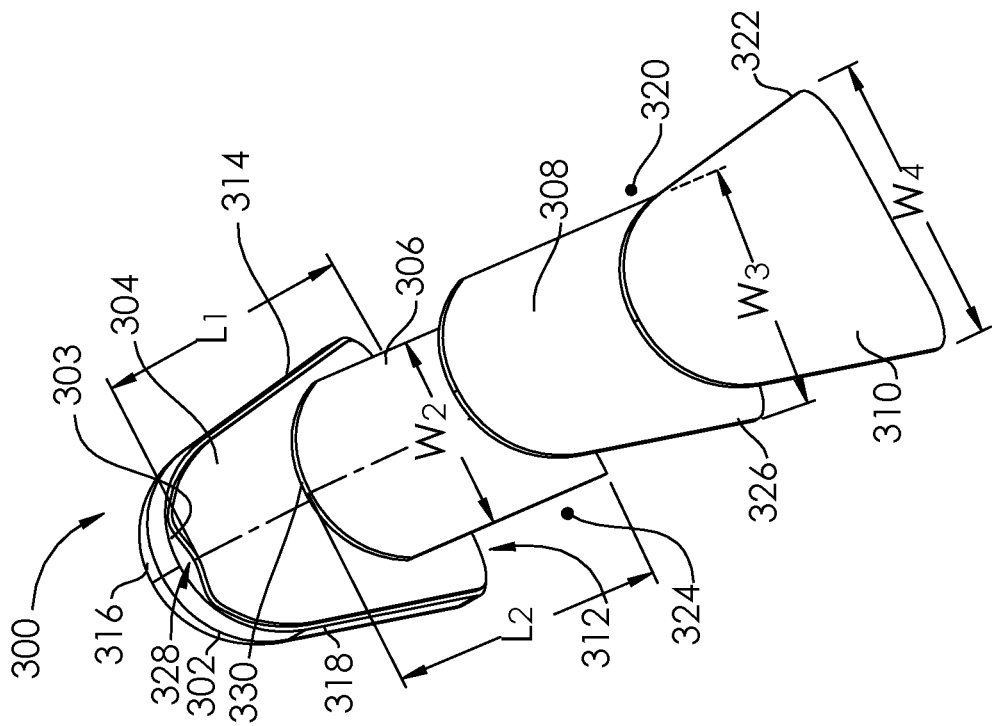
FIG. 14 is a perspective view of a system for controlling urinary incontinence according to an embodiment of the present disclosure.

FIG. 14 illustrates an exploded view of a system for controlling urinary incontinence 300 comprising a body 302, a first adhesive layer 304, a second adhesive layer 306, a third adhesive layer 308, and a fourth adhesive layer 310.

The system for controlling urinary incontinence 300 may be constructed from any of the materials described in relation to the female urinary incontinence device 10 of FIG. 1. The first adhesive layer 304 is carried on a ventral portion 303 of the body 302, and may or may not be configured to be removed from the body 302. In a first embodiment, the system for controlling urinary incontinence 300 is sold separately, for example, the body 302 is sold with the first adhesive layer disposed thereon, while each of the second adhesive layer 306, third adhesive layer 308, and fourth adhesive layer 310 is sold separately. In alternative embodiments, the second, third, and fourth adhesive layers 306, 308, 310 are each identical to each other and represent a single, packaged model (e.g., replacement adhesive layer). However, in the embodiment of FIGS. 14-16, each of the second, third, and fourth adhesive layers 306, 308, 310 have a different footprint from each other. Additionally, in the embodiment of FIGS. 14-16, each of the first, second, third, and fourth adhesive layers 304, 306, 308, 310 have a different footprint from each other. By having different footprints, the adhesive layers provide a staggered overlap which aids a user to grasp a particular adhesive layer and peel it from the adjacent adhesive layer without the need of the adhesive layer to possess a tab that extends substantially from the footprint (perimeter) of the body 302. Each of the adhesive layers 304, 306, 308, 310, when it is in its exposed state (with no adhesive layers remaining below it), is configured to provide a sealing engagement between the body 302 and the urethral meatus 38. The fourth adhesive layer 310 is configured to be removable from the third adhesive layer 308 without detaching the third adhesive layer 308 from the second adhesive layer 306, without detaching the second adhesive layer 306 from the first adhesive layer 304, and without detaching the first adhesive layer 304 from the body 302. The third adhesive layer 308 is configured to be removable from the second adhesive layer 306 without detaching the second adhesive layer 306 from the first adhesive layer 304 and without detaching the first adhesive layer 304 from the body 302. The second adhesive layer 306 is configured to be removable from the first adhesive layer 304 without detaching the first adhesive layer 304 from the body 302.

Figure 15:
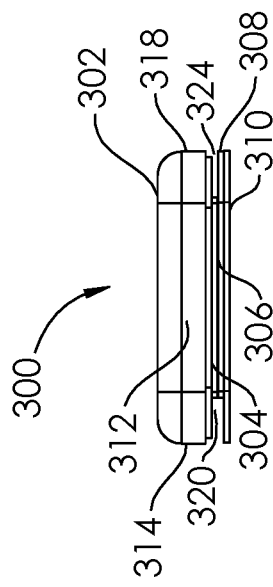
FIG. 15 is a rear view of the system for controlling urinary incontinence of FIG. 14.
Figure 16:
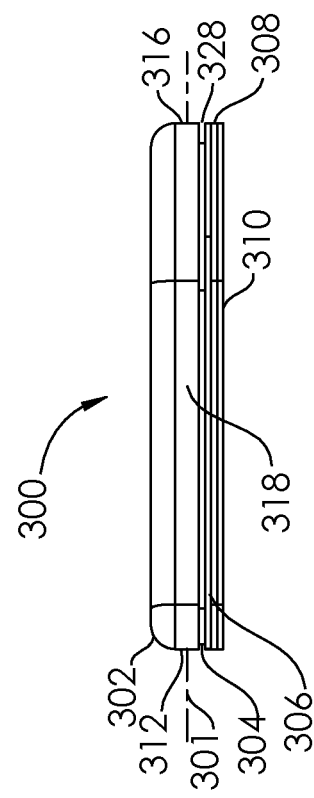
FIG. 16 is a right side view of the system for controlling urinary incontinence of FIG. 14.

The staggered layering of the adhesive layers 304, 306, 308, 310 can be seen in the exploded view of FIG. 14, and in the view of the posterior end 312 of the system for controlling urinary incontinence 300 in FIG. 15 and the view of the right lateral end 314 of the system for controlling urinary incontinence 300 in FIG. 16. The anterior end 316 is visible in FIGS. 14 and 16, and the left lateral end 318 is visible in FIGS. 14 and 15. The fourth adhesive layer 310 has a transverse width $W_4$ in relation to the longitudinal axis 301. The third adhesive layer 308 has a transverse width $W_3$ in relation to the longitudinal axis 301 that is less than the transverse width $W_4$ of the fourth adhesive layer 310. The third adhesive layer 308 has a relief area 320 at the left lateral end 318 of the system for controlling urinary incontinence 300. When it has been determined that the fourth adhesive layer 310 is to be removed (to thus expose the third adhesive layer 308), a user grasps the fourth adhesive layer 310 at a left lateral portion 322 which is adjacent the relief area 320, thus allowing the user to peel the fourth adhesive layer 310 in a left to right manner as well as a posterior to anterior manner.

The second adhesive layer 306 has a transverse width $W_2$ in relation to the longitudinal axis 301. The second adhesive layer 306 has a transverse width $W_2$ in relation to the longitudinal axis 301 that is less than the transverse width W₃ of the third adhesive layer 308. The second adhesive layer 306 has a relief area 324 at the right lateral end 314 of the system for controlling urinary incontinence 300. When it has been determined that the third adhesive layer 308 is to be removed (to thus expose the second adhesive layer 306), a user grasps the third adhesive layer 308 at a right lateral portion 326 which is adjacent the relief area 324, thus allowing the user to peel the third adhesive layer 308 in a right to left manner as well as a posterior to anterior manner. The first adhesive layer 304 has a relief area 328 at the anterior end 316 of the system for controlling urinary incontinence 300. When it has been determined that the second adhesive layer 306 is to be removed (to thus expose the first adhesive layer 304), a user grasps the second adhesive layer 306 at an anterior portion 330 which is adjacent the relief area 328, thus allowing the user to peel the second adhesive layer 306 in an anterior to posterior manner. The first adhesive layer 304 has a midline length that is less than a midline length $L_2$ of the second adhesive layer 306.

In other embodiments, the staggering of the lengths L or widths W of layers may be done in a variety of manners. Adjacent adhesive layers may decrease in widths or lengths or increase in widths or lengths. Over several adhesive layers, the dimensions may sequentially decrease at first, and then sequentially increase. Or, they may sequentially increase at first, and then sequentially decrease. The adhesive layer that is the most ventrally located at any particular moment has in at least one portion of the perimeter of the system for controlling urinary incontinence 300, an extreme outward dimension that is greater than the extreme outward dimension of the adjacent adhesive layer at that same portion of the perimeter system for controlling urinary incontinence 300.

In the embodiment of the system for controlling urinary incontinence 300 of FIGS. 14-16, including alternative embodiments thereof, the first adhesive layer 304 and/or second adhesive layer 306 and/or third adhesive layer 308 and/or fourth adhesive layer 310 may comprise one or more of the following: a hydrogel, such as Poly(2-hydroxyethyl methacrylate) (pHEMA), or a silicone hydrogel, such as a water gradient silicone hydrogel. The body 302 may comprise a foam or a silicone hydrogel, such as a water gradient silicone hydrogel.

Figure 17:
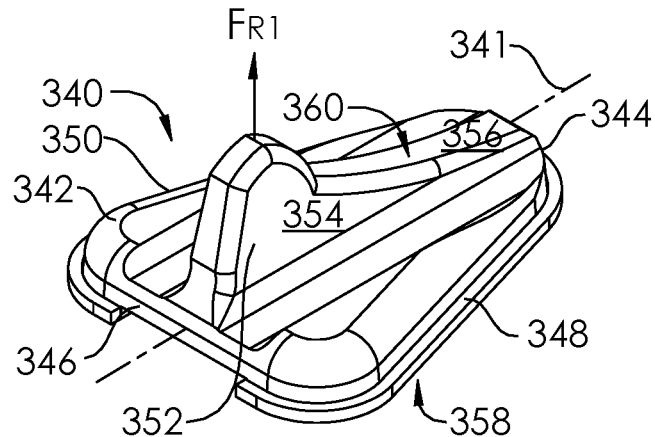
FIG. 17 is a perspective view of a system for controlling urinary incontinence according to an embodiment of the present disclosure.

FIG. 17 illustrates a system for controlling urinary incontinence 340 having a longitudinal axis 341, a body 342, an anterior end 344, a posterior end 346, a left lateral end 348, a right lateral end 350, and a longitudinal ridge 352. The longitudinal ridge 352 comprises a thicker-walled portion 354 (thickness between ventral side 358 and dorsal side 360) which is located closer to the posterior end 346 than the anterior end 344. A thinner-walled portion 356 (thickness between ventral side 358 and dorsal side 360), located generally at the anterior end 344. To remove the system for controlling urinary incontinence 340 from the general area of the vulva 36, the user grasps the longitudinal ridge 352 (e.g., between opposing fingers) and places a removal force $F_{R1}$ on the longitudinal ridge 352 thus applying a selective peeling force which begins the peel at the posterior end 346, and then moves toward the anterior end 344.

Figure 18:
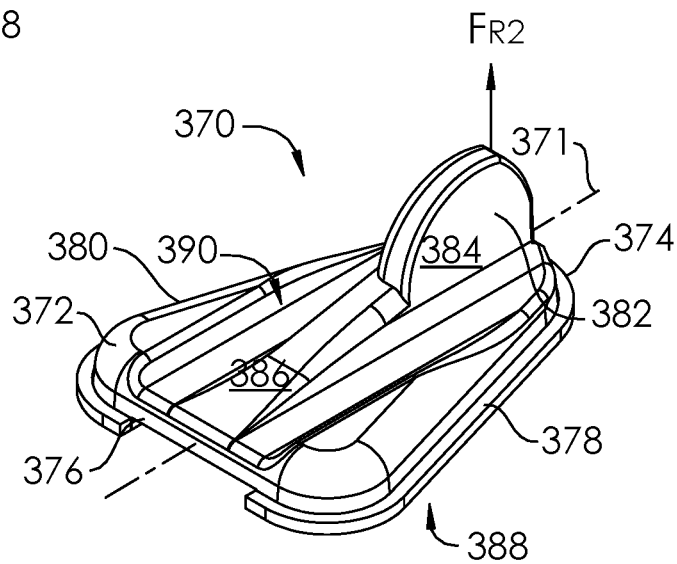
FIG. 18 is a perspective view of a system for controlling urinary incontinence according to an embodiment of the present disclosure.

FIG. 18 illustrates a system for controlling urinary incontinence 370 having a longitudinal axis 371, a body 372, an anterior end 374, a posterior end 376, a left lateral end 378, a right lateral end 380, and a longitudinal ridge 382. The longitudinal ridge 382 comprises a thicker-walled portion 384 (thickness between ventral side 388 and dorsal side 390) which is located closer to the anterior end 374 than the posterior end 376. A thinner-walled portion 386 (thickness between ventral side 388 and dorsal side 390), located generally at the posterior end 376. To remove the system for controlling urinary incontinence 370 from the general area of the vulva 36, the user grasps the longitudinal ridge 382 (e.g., between opposing fingers) and places a removal force $F_{R2}$ on the longitudinal ridge 382 thus applying a selective peeling force which begins the peel at the anterior end 374, and then moves toward the posterior end 376.

Figure 19:
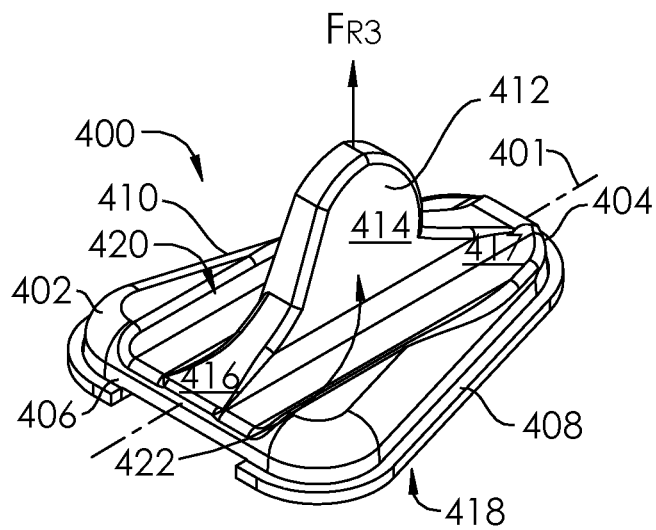
FIG. 19 is a perspective view of a system for controlling urinary incontinence according to an embodiment of the present disclosure.

FIG. 19 illustrates a system for controlling urinary incontinence 400 having a longitudinal axis 401, a body 402, an anterior end 404, a posterior end 406, a left lateral end 408, a right lateral end 410, and a longitudinal ridge 412. The longitudinal ridge 412 comprises a thicker-walled portion 414 (thickness between ventral side 418 and dorsal side 420) which is generally centrally-located between the anterior end 404 and the posterior end 406. Two thinner-walled portions 416, 417 (thickness between ventral side 418 and dorsal side 420) are located generally at the posterior end 406 and the anterior end 404, respectively. To remove the system for controlling urinary incontinence 400 from the general area of the vulva 36, the user grasps the longitudinal ridge 412 (e.g., between opposing fingers) and places a removal force $F_{R3}$ on the longitudinal ridge 412 thus applying a generally centrally-located force which is focused at a central area 422. The systems for controlling urinary incontinence 340, 370, 400 may each be constructed from any of the materials described in relation to the female urinary incontinence device 10 of FIG. 1.

Depending on the specific type of peel or removal mechanics that are desired for a particular embodiment of a system for controlling urinary incontinence one of the particular embodiments of the system for controlling urinary embodiment 340, 370, 400 of FIGS. 17-19 may be chosen so that the user simply grasps the longitudinal ridge 352, 382, 412 (or any equivalent structure such as tether, loop, etc. which is located accordingly) and pulls. The chosen mechanics for removal thus happen automatically. In some embodiments, the longitudinal ridge 352, 382, 412 may be at different location along the longitudinal axis than one or more tabs of one or more adhesive layers, so that the mechanics of the peeling of the adhesive layer(s) is purposely different than the mechanics of the removal of the system for controlling urinary embodiment 340, 370, 400. Thus, when the user removes the system for controlling urinary embodiment 340, 370, 400, the adhesive layer(s) are less likely to be inadvertently peeled off. In one embodiment, the tabs of the adhesive layers are located near an anterior end of the system for controlling urinary embodiment, while the longitudinal ridge is located near a posterior end. In another embodiment, the tabs of the adhesive layers are located near an posterior end of the system for controlling urinary embodiment, while the longitudinal ridge is located near a anterior end.

In the embodiments of the system for controlling urinary incontinence 340, 370, 400 of FIGS. 17-19, including alternative embodiments thereof, any adhesive layers may comprise one or more of the following: a hydrogel, such as Poly(2-hydroxyethyl methacrylate) (pHEMA), or a silicone hydrogel, such as a water gradient silicone hydrogel. The body 342, 372, 402 may comprise a foam or a silicone hydrogel, such as a water gradient silicone hydrogel.

Figure 20:
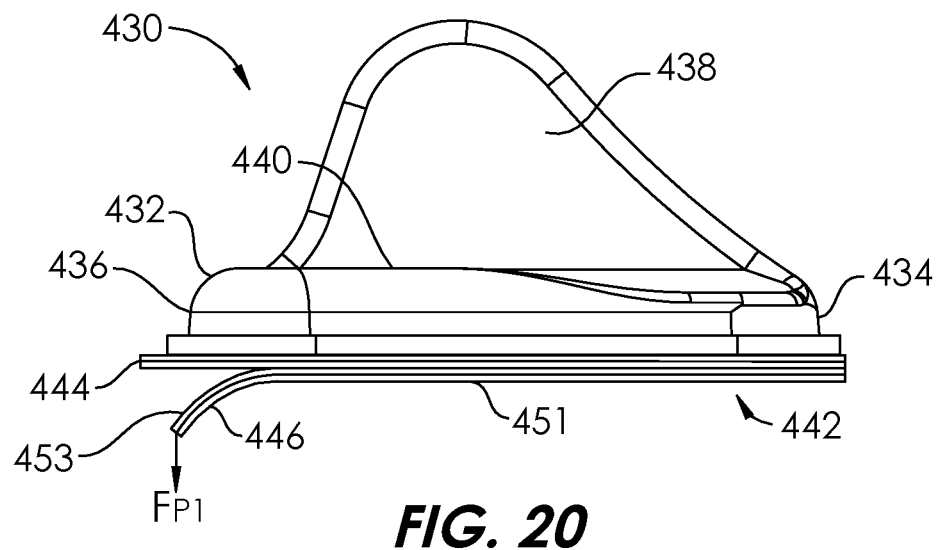
FIGS. 20 and 21 are side views of a system for controlling urinary incontinence according to an embodiment of the present disclosure, demonstrating peel forces.
Figure 21:
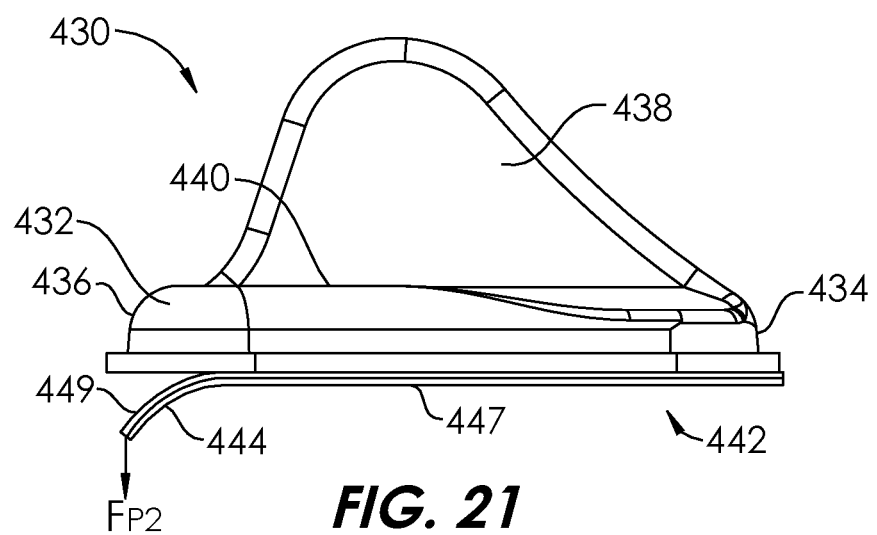
Figure 22:
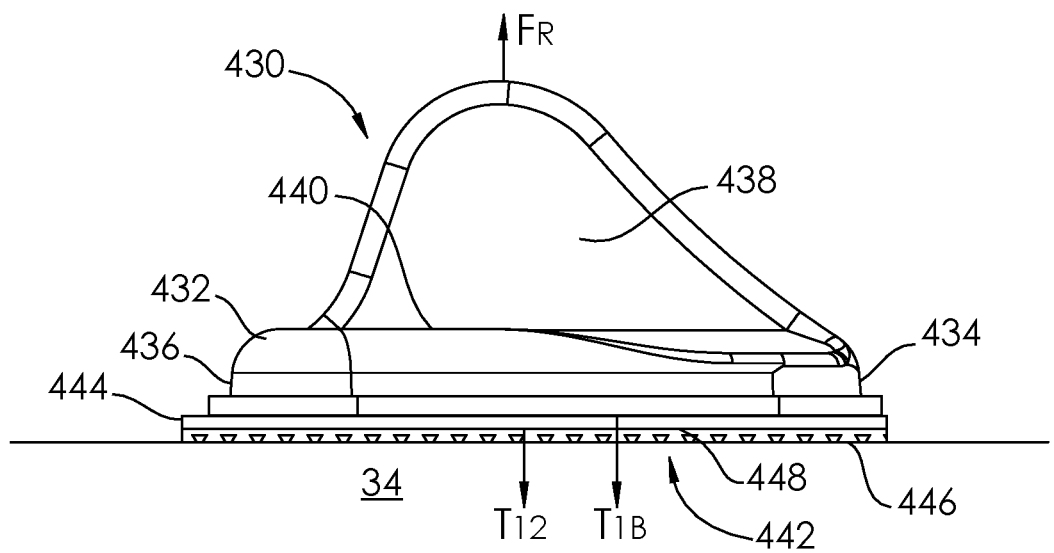
FIG. 22 is a side view of the system for controlling urinary incontinence of FIGS. 20 and 21, demonstrating a tensile or normal force.

FIGS. 20-22 illustrate a system for controlling urinary incontinence 430 having a body 432, an anterior end 434, a posterior end 436, and a longitudinal ridge 438 at a dorsal side 440. The system for controlling urinary incontinence 430 may be constructed from any of the materials described in relation to the female urinary incontinence device 10 of FIG. 1. A first adhesive layer 444 and a second adhesive layer 446 are disposed at a ventral side 442, as described with the other embodiment herein. The first adhesive layer 444 comprises an adhesive material 447 and a release liner 449. The second adhesive layer 446 comprises an adhesive material 451 and a release liner 453. The release liners 449, 453 may comprise materials and characteristics similar to the liner 222 in FIG. 9. In some embodiments, a non-removable adhesive layer may be disposed on the body 432 between the body 432 and the first adhesive layer 444, but in the embodiment of FIGS. 20-22, and so the first adhesive layer 444 may be removable from a ventral surface on the body 432 or from an intermediate/intervening adhesive layer. A first peel force $F_{P1}$ is the force required to peel the second adhesive layer 446 from the first adhesive layer 444, as illustrated in FIG. 20. A second peel force $F_{P2}$ is the force required to peel the first adhesive layer 444 from the body 432 (either from the body 432 alone, or from an intermediate adhesive layer disposed on the body), as illustrated in FIG. 21. FIG. 22 illustrates the system for controlling urinary incontinence 430 in place in a user. The removal force $F_R$ (a normal force required to remove the system for controlling urinary incontinence 430 from the vestibule floor 34 and/or urethral meatus 38) causes an equal and opposite tensile force T between the second adhesive layer 446 and the first adhesive layer 444 and also an equal and opposite tensile force T between the first adhesive layer 444 and the body 432.

The materials and/or surface areas of the body 432, first adhesive layer 444, and second adhesive layer 446 (and/or the manufacture/processing/fabrication thereof) are controlled so that $F_{P1}$ is less than $F_{P2}$. In some embodiments, $F_{P1}$ is significantly less than $F_{P2}$, so that the purposeful peeling of the second adhesive layer 446 from the first adhesive layer 444 does not cause the first adhesive layer 444 to be peeled from the body 432 (or from any intervening adhesive layer). In some embodiments, $F_{P1}$ is significantly less than $F_{P2}$, so that the purposeful peeling of the second adhesive layer 446 from the first adhesive layer 444 does not cause the first adhesive layer 444 to even begin to be peeled from the body 432 (or from any intervening adhesive layer).

The materials and surface areas of the body 432, the first adhesive layer 4, and the second adhesive layer 446 are controlled so that the tensile force $T_{12}$ at which the second adhesive layer 446 is separated from the first adhesive layer 444 is greater than the removal force $F_R$. The materials and surface areas of the body 432, the first adhesive layer 4, and the second adhesive layer 446 are also controlled so that the tensile force $T_{1B}$ at which the first adhesive layer 446 is separated from the body 432 (or from any intervening adhesive layer) is greater than the removal force $F_R$. The term "separated from the body" describes wherein a still desired (for current or eventual use) adhesive layer is pulled away enough to damage the system for controlling urinary incontinence 430, or to stop the system for controlling urinary incontinence 430 from functioning in conjunction with the desired adhesive layer. In some embodiments, the materials, geometry and fabrication of the adhesive layers 444, 446 may be controlled such that the removal force $F_R$ (i.e., from the vulva), as previously described in relation to FIGS. 17-19, is between about one $lb_f$ (pounds-force) and about five $lb_f$. In some embodiments, the adhesive layers 444, 446 may be configured such that the removal force $F_R$ is between about one $lb_f$ and about four $lb_f$. In further embodiments, the adhesive layers 444, 446 may be configured such that the removal force $F_R$ is between about one $lb_f$ and about three $lb_f$. These ranges have been found to be bearable or comfortable for a large number of users.

In the embodiments of the system for controlling urinary incontinence 430 of FIGS. 20-22, including alternative embodiments thereof, any adhesive layers may comprise one or more of the following: a hydrogel, such as Poly(2-hydroxyethyl methacrylate) (pHEMA), or a silicone hydrogel, such as a water gradient silicone hydrogel. The body 432 may comprise a foam or a silicone hydrogel, such as a water gradient silicone hydrogel.

The first peel force $F_{P1}$, as described in relation to FIG. 20, may be controlled via materials, geometry and fabrication of the adhesive layers 444, 446, such that in some embodiments, it is between about two $lb_f$ and about five $lb_f$, or in other embodiments, about three $lb_f$ and about five $lb_f$, or in other embodiments, three $lb_f$ and about four $lb_f$. Again, the materials, geometry and fabrication of the first adhesive layer 444, and second adhesive layer 446 are controlled so that $F_{P1}$ is less than $F_{P2}$.

Figure 23:
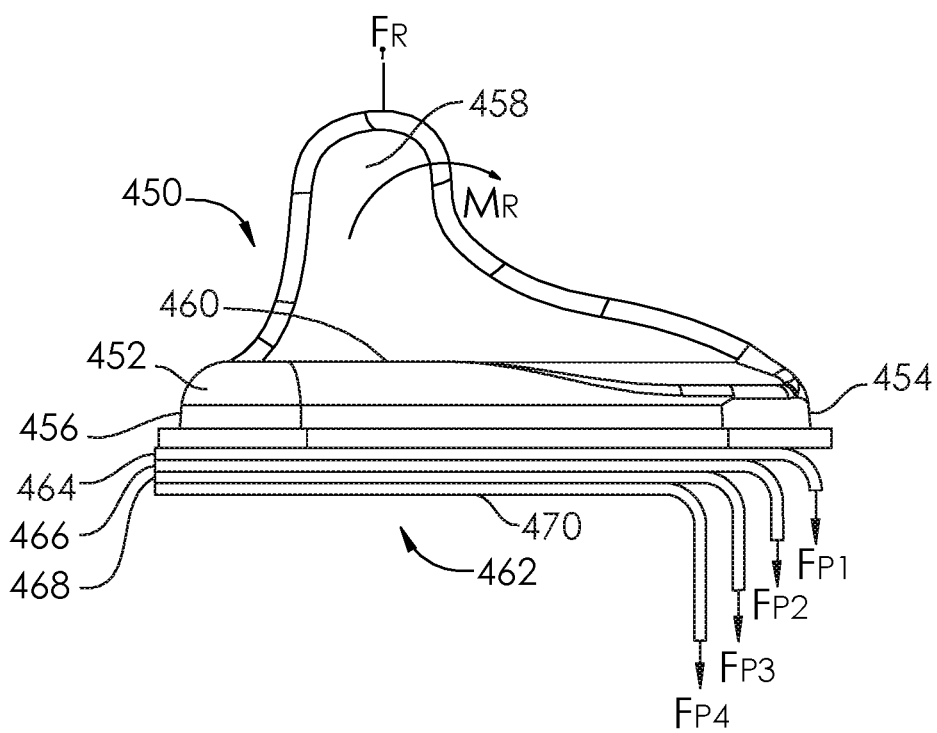
FIG. 23 is a side view of a system for controlling urinary incontinence according to an embodiment of the present disclosure, demonstrating peel forces.

FIG. 23 illustrates a system for controlling urinary incontinence 450 having a body 452, an anterior end 454, a posterior end 456, and a longitudinal ridge 458 at a dorsal side 460. The system for controlling urinary incontinence 450 may be constructed from any of the materials described in relation to the female urinary incontinence device 10 of FIG. 1. A first adhesive layer 464, a second adhesive layer 466, a third adhesive layer 468, and a fourth adhesive layer 470 are disposed at a ventral side 462, as described with the other embodiments herein. In some embodiments, a non-removable adhesive layer may be disposed on the body 452 between the body 452 and the first adhesive layer 464, and so the first adhesive layer 464 may also be configured to be removable from a ventral surface on the body 452 or from an intermediate/intervening adhesive layer.

Each of the adhesive layers 464, 466, 468, 470, when removed by the user, is configured to be peeled from the anterior end 454. However, the longitudinal ridge 458 is oriented closer to the posterior end 456, such that, when the system for controlling urinary incontinence 450 is being removed from the user, a removal force $F_R$ placed on the longitudinal ridge 458 creates a removal moment $M_R$ which facilitates both the separation of the system for controlling urinary incontinence 450 from the vestibule floor 34 and urethral meatus 38 of the user and the removal of the system for controlling urinary incontinence 450 from its location between the between the labia minora 40 and the vestibule floor 34 (see FIGS. 2-3). Peel force $F_{P4}$ is the force required to peel the fourth adhesive layer 470 from the third adhesive layer 468. Peel force $F_{P3}$ is the force required to peel the third adhesive layer 468 from the second adhesive layer 466. Peel force $F_{P2}$ is the force required to peel the second adhesive layer 466 from the first adhesive layer 464. Peel force $F_{P1}$ is the force required to peel the first adhesive layer 464 from the body 452 and/or any intervening adhesive layer. In general, the peel force of a lower (more ventral) layer is configured to be lower than the peel force(s) of any of the higher (more dorsal) layers, or lower than the cumulative peel force of all of the higher (more distal) layers as a composite. Thus, the peeling of each adhesive layer, at its chosen time for removal, does not inadvertently remove any of the remaining adhesive layers, either separately or together.

The materials and surface areas of the body 452, first adhesive layer 464, the second adhesive layer 466, the third adhesive layer 468, and the fourth adhesive layer 470 are controlled so that $F_{P4}$ is less than $F_{P3}$. In some embodiments, $F_{P4}$ is significantly less than $F_{P3}$, so that the purposeful peeling of the fourth adhesive layer 470 from the third adhesive layer 468 does not cause the third adhesive layer 468 to be peeled from the body 452 (or from any intervening adhesive layer). In some embodiments, $F_{P4}$ is significantly less than $F_{P3}$, so that the purposeful peeling of the fourth adhesive layer 470 from the third adhesive layer 468 does not cause the third adhesive layer 468 to even begin to be peeled from the body 452 (or from any intervening adhesive layer).

The materials and surface areas of the body 452, first adhesive layer 464, the second adhesive layer 466, and the third adhesive layer 468 are controlled so that $F_{P3}$ is less than $F_{P2}$. In some embodiments, $F_{P3}$ is significantly less than $F_{P2}$, so that the purposeful peeling of the third adhesive layer 468 from the second adhesive layer 466 does not cause the second adhesive layer 466 to be peeled from the body 452 (or from any intervening adhesive layer). In some embodiments, $F_{P3}$ is significantly less than $F_{P2}$, so that the purposeful peeling of the third adhesive layer 468 from the second adhesive layer 466 does not cause the second adhesive layer 466 to even begin to be peeled from the body 452 (or from any intervening adhesive layer).

The materials and surface areas of the body 452, first adhesive layer 464, and the second adhesive layer 466 are controlled so that $F_{P2}$ is less than $F_{P1}$. In some embodiments, $F_{P2}$ is significantly less than $F_{P1}$, so that the purposeful peeling of the second adhesive layer 466 from the first adhesive layer 464 does not cause the first adhesive layer 464 to be peeled from the body 452 (or from any intervening adhesive layer). In some embodiments, $F_{P2}$ is significantly less than $F_{P1}$, so that the purposeful peeling of the second adhesive layer 466 from the first adhesive layer 464 does not cause the first adhesive layer 464 to even begin to be peeled from the body 452 (or from any intervening adhesive layer).

In the embodiments of the system for controlling urinary incontinence 450 of FIG. 23, including alternative embodiments thereof, any adhesive layers may comprise one or more of the following: a hydrogel, such as Poly(2-hydroxyethyl methacrylate) (pHEMA), or a silicone hydrogel, such as a water gradient silicone hydrogel. The body 452 may comprise a foam or a silicone hydrogel, such as a water gradient silicone hydrogel.

Prior art female urinary continence devices having a single adhesive layer tend to require removal, discard, and replacement of the entire device around four times each day. One common reason for the relatively short usage life of each of these devices is degradation of the adhesive. The system for controlling urinary incontinence 450 of FIG. 23, even if no further improvements were made on the durability of the adhesive, has up to a four-time (4×) improvement in durability, thus allowing a single device to be used effectively for an entire day, and even longer. Based on the improved durability, the system for controlling urinary incontinence 450 may be configured to be discarded after about twelve to thirty-six hours of use. In some embodiments, the system for controlling urinary incontinence 450 may be configured to be discarded after about eighteen to thirty hours of use. In some embodiments, the system for controlling urinary incontinence 450 may be configured to be discarded after about twenty-one to twenty-seven hours of use.

Figure 24:
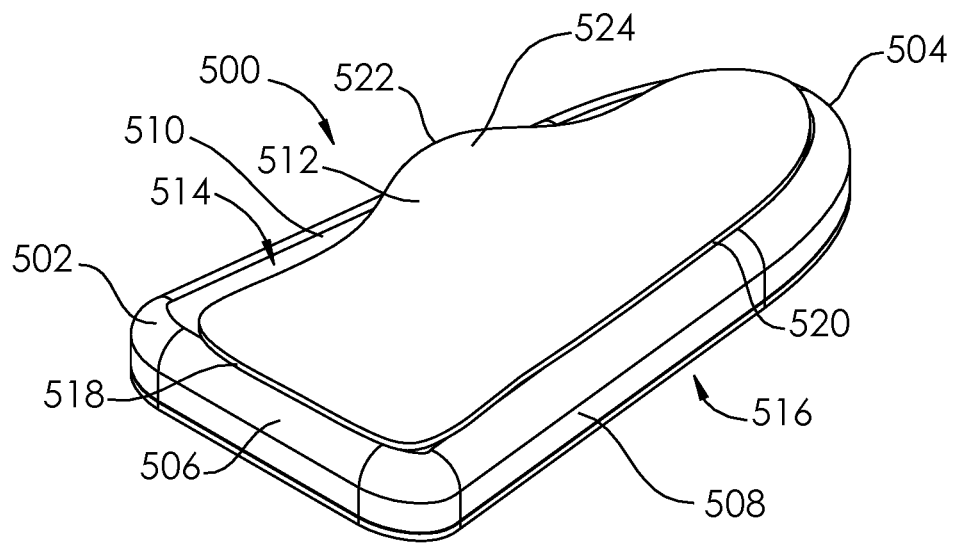
FIG. 24 is a perspective view of a system for controlling urinary incontinence according to an embodiment of the present disclosure.
Figure 25:
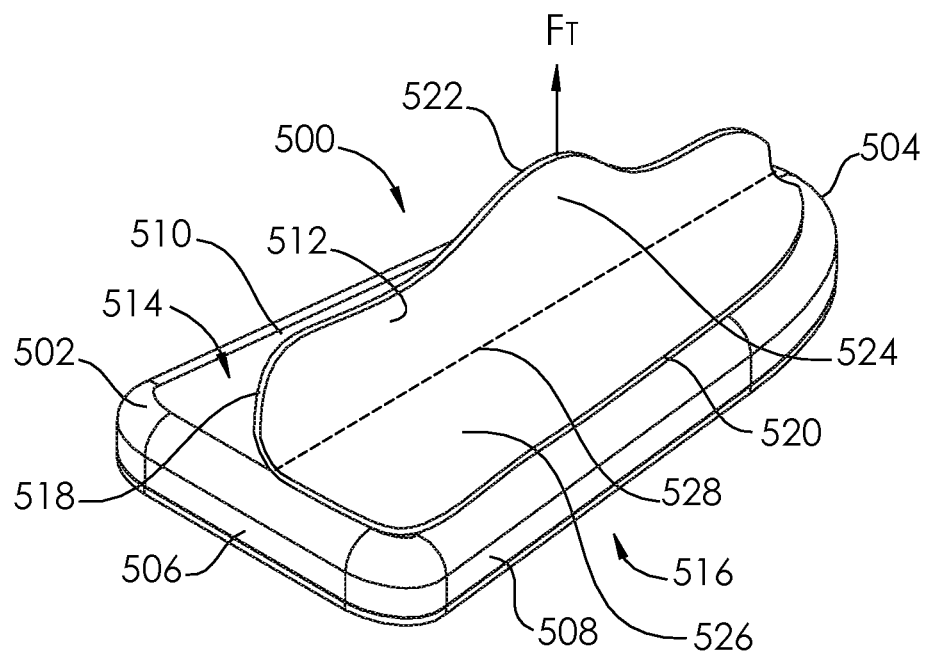
FIG. 25 is a perspective view of the system for controlling urinary incontinence of FIG. 24, being subjected to a tensile force.

FIGS. 24-25 illustrate a system for controlling urinary incontinence 500 having a body 502, an anterior end 504, a posterior end 506, a left lateral end 508, a right lateral end 510, a ventral side 516, and a resilient manipulation member 512 carried on a dorsal side 514. The system for controlling urinary incontinence 500 may be constructed from any of the materials described in relation to the female urinary incontinence device 10 of FIG. 1. The manipulation member 512 may comprise a flexible and/or foldable sheet 518 having a first end 520 which is coupled to the body 502. The manipulation member 512 extends from the dorsal side 514 of the system for controlling urinary incontinence 500 and terminates at a free second end 522. The system for controlling urinary incontinence 500 has a lower profile configuration (FIG. 24) wherein manipulation member 512 lies along the dorsal side 514 of the body 502. The system for controlling urinary incontinence 500 also has an expanded profile configuration (FIG. 25) wherein the second end 522 is displaced from the dorsal side 514 of the body 502, as a fin. A first portion 526, on one side of a midline 528 of the manipulation member 512, may be secured to the body 502 by adhesives, epoxy, heat fusing, or other known manners, while a second portion 524 is left unsecured. In one embodiment, when removing the system for controlling urinary incontinence 500, a user may grasp the manipulation member 512 (for example, with opposing fingers) at an engagement site 524 and apply a tensile force $F_T$, which moves the second portion 524 into a position generally perpendicular to a plane approximating the dorsal side 514 of the body 502. The system for controlling urinary incontinence 500 thus has a manipulation member 512 that functions similarly to the longitudinal ridge 26, 286, 352, 382, 412, 438, 458 of other embodiments described herein, but allows for a lower profile (FIG. 24) when in place in the user.

The sheet 518 may comprise a fabric or other structures, both woven and non-woven. A woven structure may serve to increase surface area to improve binding or bonding for the structures together. The first portion 526 of the manipulation member 512 may be incorporated into the body 502 or even into a (non-removable) adhesive layer. The sheet 518 may be laminated or composite and may include an intermediate "tie" layer which is incorporated into the body 512. In some embodiments, the sheet 518 comprises polyester, for example, a non-woven Sontara® 8000 series polyester, supplied by E. I. Du Pont de Nemours and Company Corporation, Wilmington, Del., USA. In some embodiments, the sheet 518 comprises polyethylene, for example, an embossed non-woven polyethylene such as Vancive® 5725P, supplied by Avery Dennison Corporation, Pasadena Calif., USA. In some embodiments, the sheet 518 comprises a polyethylene foam, for example, as supplied by Sekisui, as described herein. In some embodiments, the sheet 518 comprises a non-woven blend of cellulose and polyester. In some embodiments, the sheet 518 comprises collagen. In some embodiments, the manipulation member 512 may be scored or creased along the midline 528, such that the second portion 524 extends substantially perpendicular to the dorsal side 514 of the body 502. In some embodiments, the system for controlling urinary incontinence 500 may include removable adhesive layers, such as those described herein.

Figure 26:
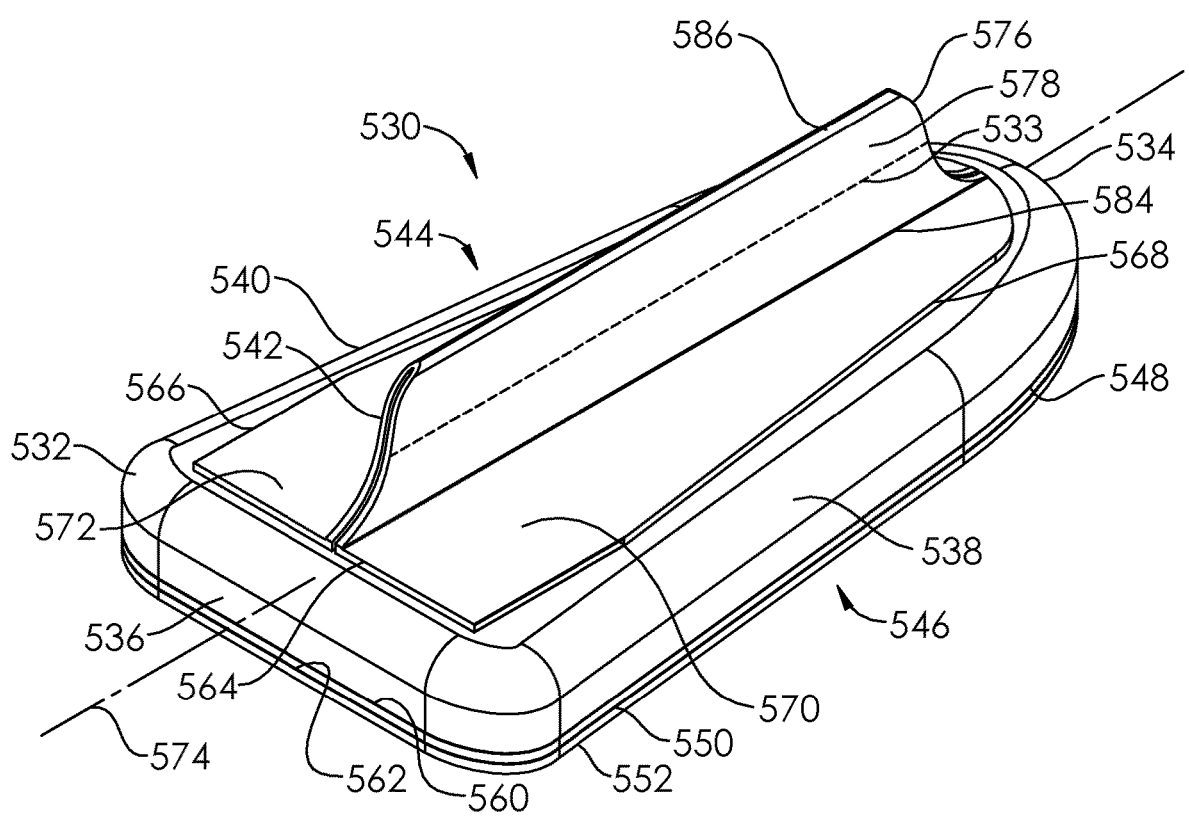
FIG. 26 is a perspective view of a system for controlling urinary incontinence according to an embodiment of the present disclosure.
Figure 27:
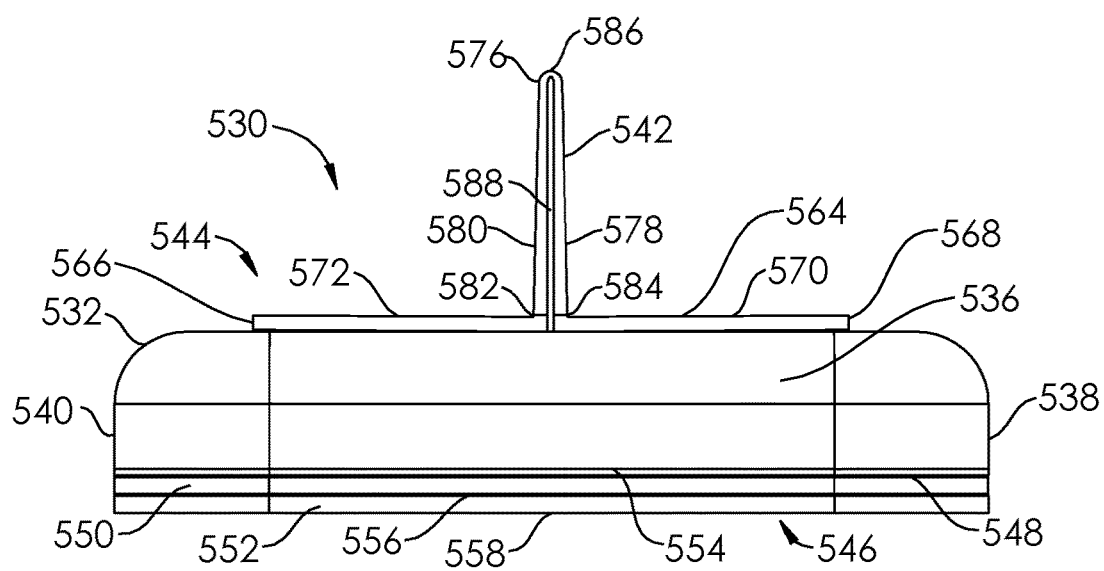
FIG. 27 is a posterior view of the system for controlling urinary incontinence of FIG. 26.

FIGS. 26-27 illustrate a system for controlling urinary incontinence 530 having a body 532, an anterior end 534, a posterior end 536, a left lateral end 538, a right lateral end 540, a ventral side 546, and a manipulation member 542 carried on a dorsal side 544. The system for controlling urinary incontinence 530 may be constructed from any of the materials described in relation to the female urinary incontinence device 10 of FIG. 1 or the system for controlling urinary incontinence 500 of FIG. 24. The system for controlling urinary incontinence 530 includes a first adhesive surface 548 carried on a ventral surface 554 the body 532, a first removable adhesive layer 550 and second removable adhesive layer 552. The first removable adhesive layer 552 includes a second adhesive surface 556, and the second removable adhesive layer 552 includes a third adhesive surface 558. The third surface 558 of the second removable adhesive layer 552 is configured to be used initially by the user. The second removable adhesive layer 552 is configured to be removed from the first removable adhesive layer 550, for example, when the adhesion of the third adhesive surface 558 is no longer sufficient or desirable (e.g., no longer is capable of producing desired removal forces). The second adhesive surface 556 of the first removable adhesive layer 550 is then configured to be used by the user. The first removable adhesive layer 550 is configured to subsequently be removed from the first adhesive surface 548, for example, when the adhesion of the second adhesive surface 556 is no longer sufficient or desirable. The first adhesive surface 548 is then configured to be used by the user. The body 532 having the first adhesive surface 548 may then be discarded when the first adhesive surface 548 is no longer sufficient or desirable. Each of the first and second removable adhesive layers 550, 552 may include a liner 560, 562, for example, to provide a controlled peel force.

The manipulation member 542 has a fin-shape, and is formed from a single sheet 564 having a first lateral end 566 and a second lateral end 568. A first portion 570 of the sheet 564 is secured to the body 532 left of a longitudinal axis 574 and a second portion 572 of the sheet 564 is secured to the body 532 right of the longitudinal axis 574. Each of the portions 570, 572 may be secured to the body 532 by adhesive, epoxy, or may be heat formed or molded into the body 532. In some embodiments, the portions 570, 572 may be woven into the body 532, or into a woven layer that is embedded within the body 532. A central portion 576 of the sheet 564 includes a left side 578 and a right side 580, which may be formed by folds, such as base folds 582, 584 and an intermediate fold 586. In other embodiments, one or more of the folds 582, 584, 586 may include scoring on one or more face of the sheet 564, which may aid the foldability. In other embodiments, one or more of the folds 582, 584, 586 may include intermittent longitudinal (broken) cuts through the sheet 564, which may aid the foldability. In some embodiments, in place of the folds 582, 584, 586 may instead by small radius curves (e.g., about 90°) which are formed into the sheet 564.

With the first and second portions 570, 572 of the sheet 564 secured to the body 532, the left side 578 and right side 580 of the central portion 576 of the sheet 564 need not be secured to each other by any means, (e.g., in the space 588 between them), as they are integral to each other, both being part of the sheet 564. However, in some embodiments, an adhesive or epoxy may be placed within the space 588 to either further secure the left side 578 and right side 580 of the central portion 576 and/or to stiffen the central portion 576. In some embodiments, the central portion 576 may purposely be left flexible so that it may be folded to one or the other side of the body 532. Or, in other embodiments, if the space 588 is non-bonded, the central portion 576 may be opened and folded along lines 533 (on each side) to bring the fold 586 straight down to toward the longitudinal axis 574 of the body 532. However, like the ridge 26 of the body 12 in FIG. 1, the manipulation member 542 provided by the central portion 576 is configured to comfortably reside between the labia minora 40 (FIG. 3) when worn (e.g., when in place) on the user. By grasping the manipulation member 542 with two opposing fingers, the user may apply a removal force in either a dorsal direction, a posterior direction, or a combination of both, or may apply a removal moment, for some peeling effect, as described in relation to FIG. 23. Though one particular shape is displayed in FIG. 26, a number of shapes are contemplated for the manipulation member 542, including shapes similar to, but not limited to, the shapes of the longitudinal ridges 352, 382, 412 in FIGS. 17-19. The sheet 564, includes contours which, when secured to the body 532, match or follow the contouring of the body 532. For example, the anterior portion of the secured sheet 564 has a smaller width than the posterior portion, and tapers anteriorly, much like the body 532. By the use of a single sheet 564 to form the manipulation member 542, the body 532 need not be molded in a more complex shape (as in FIG. 1), and may have a simpler, more two-dimensional form. In some embodiments, the body 532 need not be molded at all, and may instead be cut from sheet material or even from foam tape. More examples will be provided in the following embodiments.

Figure 28:
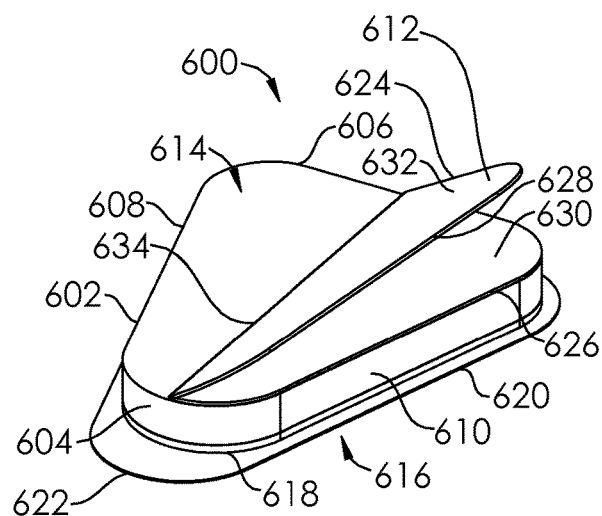
FIG. 28 is a perspective view of a system for controlling urinary incontinence according to an embodiment of the present disclosure.

FIG. 28 illustrates a system for controlling urinary incontinence 600 having a body 602, an anterior end 604, a posterior end 606, a left lateral end 608, a right lateral end 610, a ventral side 616, and a manipulation member 612 carried on a dorsal side 614. The system for controlling urinary incontinence 600 may be constructed from any of the materials described in relation to the female urinary incontinence device 10 of FIG. 1 or the system for controlling urinary incontinence 500 of FIG. 24. The body 602 may comprise a foam base which is cut from a sheet of material, and includes one or more adhesive layers 618 disposed on the ventral side 616. The system for controlling urinary incontinence 600 is shown in FIG. 28 in its packaged configuration, and has a removable protective sheet 620 covering the adhesive layer 618. The protective sheet 620 may comprise a paper or cardboard, or a polyester sheet. The protective sheet 620 may be coated with a release coating to ease removal from the adhesive layer 618. Any of the embodiments described herein may include a protective sheet similar to the protective sheet 620 for covering the most ventral adhesive surface while packaged and prior to use. Though only one adhesive layer 618 is shown in FIG. 28, the system for controlling urinary incontinence 600 may include multiple removable adhesive layers, as in other embodiments herein. The protective sheet 620 is shown having dimensions that are somewhat larger than the dimensions of the body 602, this allowing access for one or more of the ends to be grasped for peeling the protective sheet 620 off from the adhesive layer 618. The protective sheet 620 has a projection 622, or tab, at its anterior end to aid in this purpose.

The manipulation member 612 is formed from a single sheet 624 having a first lateral end 626 and a second lateral end 628. A first portion 630 of the sheet 624 is secured to the body 602 at one side and a second portion 632 (e.g., a "fin") is configured for grasping. The first portion 630 may be secured to the body 602 by adhesive, epoxy, or may be heat formed or molded into the body 602. In some embodiments, the first portion 630 may be woven into the body 602, or into a woven layer that is embedded within the body 602.

Figure 29:
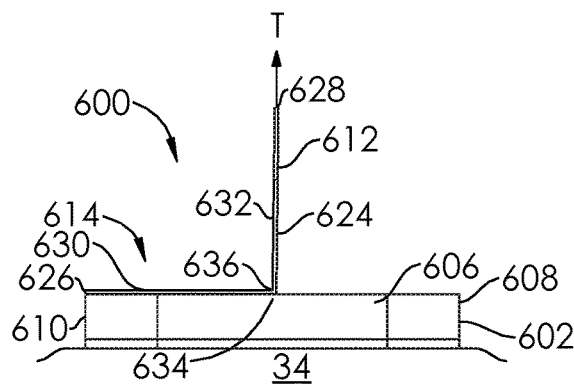
FIG. 29 is a posterior view of the system for controlling urinary incontinence of FIG. 28, being subjected to a tensile force while being removed from a user.

In FIG. 29, the system for controlling urinary incontinence 600 is in place adjacent the vestibule 34 of a user. During removal, the user grasps the second portion 632 between opposing fingers and pulls, placing a tensile force T on the second portion 632, and a removal force on the system for controlling urinary incontinence 600, thus separating the adhesive layer 618 from the urethral meatus 38 and/or the vestibule 34. The tensile force T is transferred to a region in the vicinity of a mid-line 634 adjacent a fold 636 in the sheet 624. The system for controlling urinary incontinence 600 is constructed from simple, sheet materials, including the body 602, the adhesive layer(s) 618, the sheet 624 comprising the manipulation member 612, and the removable protective sheet 620, thus the manufacturing process is simplified. Alternatively, the one or more adhesive layers may be coated onto the body 602, instead of being sheet material. The manufacturing steps may include only a) procuring a particular sheet material, b) cutting the sheet material to a desired shape, c) attaching one cut sheet shape to another cut sheet shape, and d) adding adhesive to one or more of the sheets. Thus, the system for controlling urinary incontinence 600 may be efficiently mass-produced.

Figure 30:
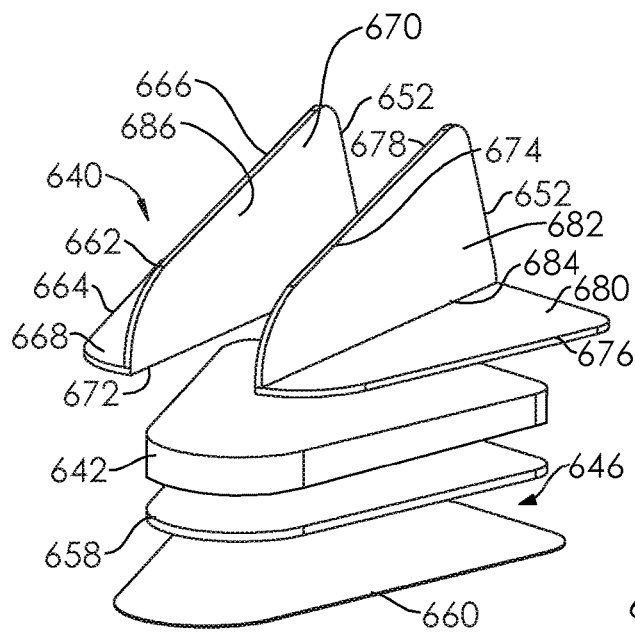
FIG. 30 is an exploded view of a system for controlling urinary incontinence according to an embodiment of the present disclosure.
Figure 31:
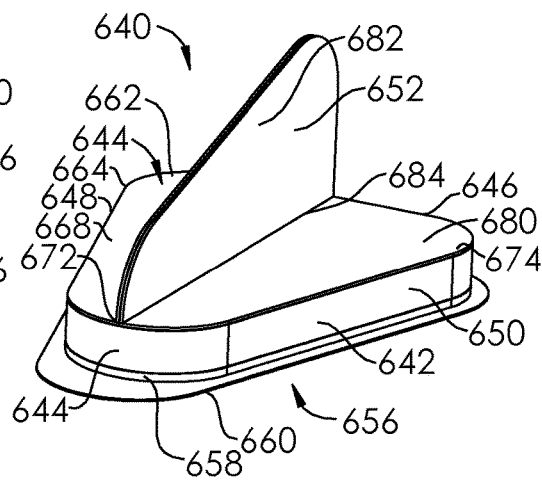
FIG. 31 is a perspective view of the system for controlling urinary incontinence of FIG. 30.

FIGS. 30-31 illustrate a system for controlling urinary incontinence 640 having a body 642, an anterior end 644, a posterior end 646, a left lateral end 648, a right lateral end 650, a ventral side 656, and a manipulation member 652 carried on a dorsal side 644. The system for controlling urinary incontinence 640 may be constructed from any of the materials described in relation to the female urinary incontinence device 10 of FIG. 1 or the system for controlling urinary incontinence 500 of FIG. 24. The body 642 may comprise a foam base which is cut from a sheet of material, and includes one or more adhesive layers 658 (removable and/or non-removable) disposed on the ventral side 656. The system for controlling urinary incontinence 640 is shown in FIG. 30 in an exploded view and in FIG. 31 in its packaged configuration, and is packaged or supplied with a removable protective sheet 660 covering the adhesive layer(s) 658. The protective sheet 660 may comprise a paper or cardboard, or a polyester sheet. The protective sheet 660 may be coated with a coating to ease removal from the adhesive layer 658. Though only one adhesive layer 658 is shown in FIGS. 30-31, the system for controlling urinary incontinence 640 may include multiple removable adhesive layers, as in other embodiments herein.

The system for controlling urinary incontinence 640 of FIGS. 30-31, like the system for controlling urinary incontinence 600 of FIGS. 28-29, can be manufactured in a simple and efficient manner using predominantly sheet materials. The manipulation member 652, however, comprises two sheets instead of one. A first sheet 662 has a first end 664 and a second end 666, and a first portion 668 and a second portion 670, separated by a fold 672. The first portion 668 of the first sheet 662 is secured to the body 642 at a first side and the second portion 670 (e.g., a "fin") is configured for grasping, though only on one (external, lateral) side. The first portion 668 may be secured to the body 642 by adhesive, epoxy, or may be heat formed or molded into the body 642. In some embodiments, the first portion 668 may be woven into the body 642, or into a woven layer that is embedded within the body 642. A second sheet 674 has a first end 676 and a second end 678, and a first portion 680 and a second portion 682, separated by a fold 684. The first portion 680 of the second sheet 674 is secured to the body 642 at a second side (opposite the first side) and the second portion 682 (e.g., a "fin") is configured for grasping, though only on one (external, lateral) side, as the second portion 682 of the second sheet 674 is configured to couple to the second portion 670 of the first sheet 662. The first portion 680 of the second sheet 674 may be secured to the body 642 by adhesive, epoxy, or may be heat formed or molded into the body 642. In some embodiments, the first portion 680 may be woven into the body 642, or into a woven layer that is embedded within the body 642. The second portion 682 of the second sheet 674 may be secured to the second portion 670 of the first sheet 662 using adhesive, hot melt or epoxy, or by thermal securement, or even by fasteners (staples, sewing, suturing, riveting, etc.). In the case of adhesive, hot melt or epoxy joining, the material used to adhere the two portions may be applied between the two portions on one or both of the internal faces 686 (only one is visible in FIG. 30). In FIG. 31, the first portion 668 is shown secured at a portion of the body 642 toward the left lateral end 648, and the first portion 680 is shown secured at a portion of the body 642 toward the right lateral end 650. As previously described, the materials of the body 502, 532, 602, 642 of any of the embodiments of FIGS. 24-31 may comprise foam materials such as HYPOL 2002 or HYPOL 6000, polyvinyl chloride foam, or polyolefin foam. In some embodiments, a polyvinyl chloride foam may be utilized, such as Gaska® tape supplied by Gaska Tape, Inc., Elkhart, Ind., USA, and may have a density of between about 80 kg/m$^3$ and about 160 kg/m$^3$, or in other embodiments between about 95 kg/m$^3$ and about 130 kg/m$^3$, or in other embodiments, about 112 kg/m$^3$. In some embodiments, a polyolefin foam may be utilized, such as Softlon™ or Volara® foams, supplied by Sekisui Voltek LLC Corporation, Lawrence, Mass., USA.

Additionally, and as previously described, the materials of the sheets 518, 564, 624, 662, 674 may comprise polyester, for example, a non-woven Sontara® 8000 series polyester, supplied by E. I. Du Pont de Nemours and Company Corporation, Wilmington, Del., USA, or a polyethylene, for example, an embossed non-woven polyethylene such as Vancive® 5725P, supplied by Avery Dennison Corporation, Pasadena Calif., USA, or a polyethylene foam, for example, as supplied by Sekisui, as described herein, or a non-woven blend of cellulose and polyester. The body 502, 532, 602, 642 or sheet 518, 564, 624, 662, 674 may in some embodiments be die-cut, thus further increasing the efficiency of producing them.

Any of the embodiments of the system for controlling urinary incontinence described herein may additionally comprise an anti-bacterial coating, to further provide a system which may remain on the user for a prolonged amount of time.

From the foregoing, the features of the present invention will be readily appreciated. The incontinence device in accordance with the present invention provides effective management of female urinary incontinence, such as stress incontinence, without the inconvenience and discomfort associated with prior art urine collection devices and absorbent pads. The present invention is easy to use and comfortable to wear. It is easily shaped and sized to fit each individual user's anatomy with optimum effectiveness and comfort. Easily and inexpensively manufactured, the present invention can be made as a disposable item.

While embodiments have been shown and described, various modifications may be made without departing from the scope of the inventive concepts disclosed herein.

What is claimed is:

1. A system for managing female incontinence comprising:
   a non-molded first sheet configured to fit between the labia minora and the vestibule floor of a female human subject, the first sheet comprising a substantially planar dorsal surface and a substantially planar ventral surface, the substantially planar ventral surface of the first sheet configured for placement over the vestibule floor around the urethral meatus of the subject;
   an adhesive layer comprising a substantially planar dorsal surface and a substantially planar ventral surface, the substantially planar dorsal surface of the adhesive layer coupled to the substantially planar ventral surface of the first sheet, and the substantially planar ventral surface of the adhesive layer configured to provide a sealing engagement between the first sheet and the urethral meatus; and a non-molded second sheet having a first portion and second portion, the first portion of the second sheet coupled to the substantially planar dorsal surface of the first sheet and the second portion of the second sheet forming a dorsally-extending fin configured to be grasped to apply a removal force to the first sheet and adhesive layer.

2. The system of claim 1, wherein the first portion of the second sheet includes a first end of the second sheet and the second portion of the second sheet includes a second end of the second sheet, and wherein the first end of the second sheet is coupled to the substantially planar dorsal surface of the first sheet at a first lateral end of the first sheet.

3. The system of claim 2, further comprising a third sheet having a first end and a second end, the first end of the third sheet coupled to the substantially planar dorsal surface of the first sheet at a second lateral end of the first sheet, opposite the first lateral end.

4. The system of claim 3, wherein the second end of the third sheet is coupled to the second end of the second sheet.

5. The system of claim 1, wherein the first sheet comprises a foam.

6. The system of claim 5, wherein the first sheet comprises polyvinyl chloride foam.

7. The system of claim 5, wherein the first sheet comprises polyolefin foam.

8. The system of claim 1, wherein the first sheet comprises cellulose.

9. The system of claim 1, wherein the first sheet comprises a woven layer.

10. The system of claim 1, wherein the first sheet comprises a foam tape.

11. The system of claim 1, wherein the second sheet further comprises a third portion coupled to the substantially planar dorsal surface of the first sheet, and wherein the second portion of the second sheet is located between the first portion of the second sheet and the third portion of the second sheet.

12. The system of claim 11, wherein the first portion of the second sheet includes a first end of the second sheet and the third portion of the second sheet includes a second end of the second sheet, and wherein the first end of the second sheet is coupled to the substantially planar dorsal surface of the first sheet at a first lateral end of the first sheet, and the second end of the second sheet is coupled to the substantially planar dorsal surface of the first sheet at a second lateral end of the first sheet, opposite the first lateral end.

13. The system of claim 12, wherein the dorsally-extending fin of the second portion of the second sheet comprises a left side, a right side, and an elongate central fold between the left side and the right side.

14. The system of claim 1, wherein the adhesive layer comprises a hydrogel.

15. The system of claim 1, wherein the adhesive layer comprises pHEMA.

16. The system of claim 1, wherein the adhesive layer comprises a silicone hydrogel.

17. The system of claim 1, wherein the first sheet is a die-cut sheet.

18. The system of claim 1, wherein the adhesive layer is coupled to the first sheet by an intermediate "tie" layer.

19. The system of claim 1, wherein the adhesive layer is removable from the first sheet.

20. The system of claim 1, wherein the second sheet comprises a fabric.

* * * * *